US009381297B2

(12) United States Patent
Brown et al.

(10) Patent No.: US 9,381,297 B2
(45) Date of Patent: Jul. 5, 2016

(54) SEALED INFUSION DEVICE WITH ELECTRICAL CONNECTOR PORT

(71) Applicant: Tandem Diabetes Care, Inc., San Diego, CA (US)

(72) Inventors: Justin Brown, San Diego, CA (US); Donald Ludolph, San Diego, CA (US); Philip Lamb, San Diego, CA (US); Anthony Barghini, San Diego, CA (US); Sean Saint, San Diego, CA (US); Marcus Julian, San Diego, CA (US); Robert Eastridge, San Diego, CA (US); Michael Rosinko, Anaheim, CA (US); Michael Michaud, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 260 days.

(21) Appl. No.: 13/827,707

(22) Filed: Mar. 14, 2013

(65) Prior Publication Data
US 2013/0331790 A1 Dec. 12, 2013

Related U.S. Application Data

(60) Provisional application No. 61/656,967, filed on Jun. 7, 2012.

(51) Int. Cl.
*A61M 5/142* (2006.01)
(52) U.S. Cl.
CPC ........... *A61M 5/142* (2013.01); *A61M 5/14244* (2013.01); *A61M 2205/3569* (2013.01)
(58) Field of Classification Search
CPC ........... A61M 5/14244; A61M 5/142; A61M 2205/3569

USPC .............. 604/151, 246, 65; 439/89, 271, 272, 439/278, 57, 358, 606, 607.413
See application file for complete search history.

(56) References Cited

U.S. PATENT DOCUMENTS

| 5,338,157 A | 8/1994 | Blomquist |
| 5,368,562 A | 11/1994 | Blomquist |
| 5,485,408 A | 1/1996 | Blomquist |

(Continued)

FOREIGN PATENT DOCUMENTS

| CN | 202633634 U | * 12/2012 |
| WO | WO 2009/113060 A2 | 9/2009 |
| WO | WO 2010-022136 A2 | 2/2010 |

OTHER PUBLICATIONS

Search Report dated Sep. 5, 2013 for PCT Application No. PCT/US2013/044289 filed Jun. 5, 2013, 11 pages.

(Continued)

*Primary Examiner* — Justin Jonaitis
*Assistant Examiner* — Christopher Brunjes
(74) *Attorney, Agent, or Firm* — Patterson Thuente Pedersen, P.A.

(57) ABSTRACT

A portable medical device includes an interface for accepting a power supply and enabling data transfer while still connected to a human body. The interface may include a universal serial bus interface and may be coupled to a data isolation chip and a power isolation chip. A power controlling processor may determine how the supplied power, e.g., voltage, is supplied to other components within the infusion device. Additional circuitry within the system may provide a secure power transfer within the device to ensure user safety and ensure that a high frequency noise is properly attenuated.

14 Claims, 16 Drawing Sheets

(56) References Cited

U.S. PATENT DOCUMENTS

| | | | |
|---|---|---|---|
| 5,658,250 A | 8/1997 | Blomquist et al. | |
| 5,676,651 A | 10/1997 | Larson, Jr. et al. | |
| 5,688,232 A | 11/1997 | Flower | |
| 5,935,099 A | 8/1999 | Peterson et al. | |
| 5,941,846 A | 8/1999 | Duffy et al. | |
| 6,024,539 A | 2/2000 | Blomquist | |
| 6,241,704 B1 | 6/2001 | Peterson et al. | |
| 6,254,569 B1 | 7/2001 | O'Donnell et al. | |
| 6,475,180 B2 | 11/2002 | Peterson et al. | |
| 6,565,802 B1 | 5/2003 | Hanley et al. | |
| 6,639,381 B2 | 10/2003 | Tamura et al. | |
| 6,749,587 B2 * | 6/2004 | Flaherty | A61M 5/14248 604/151 |
| 6,986,867 B2 | 1/2006 | Hanley et al. | |
| 7,095,210 B2 | 8/2006 | Tamura et al. | |
| 7,136,701 B2 | 11/2006 | Greatbatch et al. | |
| 7,187,528 B2 | 3/2007 | Talbot et al. | |
| 7,347,836 B2 | 3/2008 | Peterson et al. | |
| 7,455,552 B1 * | 11/2008 | Fang | H05K 3/284 439/606 |
| 7,460,350 B2 | 12/2008 | Talbot et al. | |
| 7,553,291 B2 | 6/2009 | Duffy et al. | |
| 7,654,976 B2 | 2/2010 | Peterson et al. | |
| 7,753,713 B2 * | 7/2010 | Neale, III | H01R 13/64 439/357 |
| 7,976,778 B2 | 7/2011 | Drucker et al. | |
| 8,030,058 B1 | 10/2011 | Benedict et al. | |
| 8,030,891 B2 | 10/2011 | Welsch et al. | |
| 8,118,770 B2 | 2/2012 | Galley et al. | |
| 8,126,728 B2 | 2/2012 | Dicks et al. | |
| 8,126,729 B2 | 2/2012 | Dicks et al. | |
| 8,126,730 B2 | 2/2012 | Dicks et al. | |
| 8,126,732 B2 | 2/2012 | Dicks et al. | |
| 8,126,733 B2 | 2/2012 | Dicks et al. | |
| 8,126,734 B2 | 2/2012 | Dicks et al. | |
| 8,140,356 B2 | 3/2012 | Dicks et al. | |
| 8,155,982 B2 | 4/2012 | Dicks et al. | |
| 8,211,364 B2 | 7/2012 | Drucker et al. | |
| 8,234,128 B2 | 7/2012 | Martucci et al. | |
| 8,236,242 B2 | 8/2012 | Drucker et al. | |
| 8,257,652 B2 | 9/2012 | Drucker et al. | |
| 8,257,653 B2 | 9/2012 | Drucker et al. | |
| 8,451,230 B2 | 5/2013 | Celentano et al. | |
| 2006/0189895 A1 | 8/2006 | Neel et al. | |
| 2007/0017505 A1 * | 1/2007 | Lipp | A61M 15/02 128/200.16 |
| 2008/0065007 A1 | 3/2008 | Peterson et al. | |
| 2008/0065016 A1 | 3/2008 | Peterson et al. | |
| 2008/0103554 A1 | 5/2008 | Dicks et al. | |
| 2009/0256527 A1 | 10/2009 | Welsch et al. | |
| 2010/0004595 A1 * | 1/2010 | Nguyen | A61B 18/04 604/99.04 |
| 2010/0192686 A1 | 8/2010 | Kamen et al. | |
| 2010/0331646 A1 * | 12/2010 | Hoss | A61B 5/14503 600/347 |
| 2011/0071465 A1 | 3/2011 | Wang et al. | |
| 2011/0074120 A1 * | 3/2011 | Namey, Jr. | B29C 45/14311 277/650 |
| 2011/0092894 A1 | 4/2011 | Mcgill et al. | |
| 2011/0093285 A1 | 4/2011 | Dicks et al. | |
| 2011/0093286 A1 | 4/2011 | Dicks et al. | |
| 2011/0119087 A1 | 5/2011 | Drucker et al. | |
| 2011/0125085 A1 | 5/2011 | Mcgill et al. | |
| 2011/0125530 A1 | 5/2011 | Drucker et al. | |
| 2011/0144586 A1 | 6/2011 | Michaud | |
| 2011/0196248 A1 | 8/2011 | Grunwald | |
| 2012/0022452 A1 * | 1/2012 | Welsch | A61M 5/142 604/151 |

OTHER PUBLICATIONS

International Preliminary Report on Patentability dated Dec. 9, 2014 for PCT Application No. PCT/US2013/044289 filed Jun. 5, 2013, 8 pages.

Search Report dated Mar. 14, 2016 for European Application No. 13800289.4, 6 pages.

* cited by examiner

SEALED INFUSION DEVICE WITH ELECTRICAL CONNECTOR PORT

RELATED APPLICATION

The present application claims the benefit of U.S. Provisional Application No. 61/656,967 filed Jun. 7, 2012, which is incorporated herein in its entirety by reference.

BACKGROUND

Electrically-powered portable devices often include portable power sources, such as batteries, that must be recharged periodically. Many such devices also provide communications to a host device or other associated machinery, so as to exchange data relating to device operation, maintenance history, and the like. Recharging a portable device and exchanging data through a host device, which provides a power source, often involves receiving electrical power and communicating data over a single connection. Such connections may comprise, for example, a Universal Serial Bus (USB) connector coupling the portable device to a host computer or a USB hub. The portable device often must be constructed for operation so it is isolated from the source that provides electrical power for operation and for charging, and often must be isolated as well from the source of data exchange and communications. Such portable devices may include laboratory devices, portable test equipment, and portable user devices.

One example of a portable device such as described above is a device that involves the delivery of fluids. There are many applications in academic, industrial, and medical fields, as well as others, that involve devices capable of accurately and controllably delivering fluids, including liquids and gases, that have a beneficial effect when administered in known and controlled quantities. This is particularly true in the medical field, where treatments for many patients include the administration of a known amount of a substance at predetermined intervals. For example, the treatment of diabetes involves just such a regimented dosage of medicaments such as insulin. In addition, diabetes is one of a few medical indications wherein the patient routinely administers the medicament (such as insulin) to themselves by a subcutaneous modality, such as, e.g., via a hypodermic syringe injection or an ambulatory infusion device, or pump. This is an example wherein providing a patient with the safe, reliable, and comfortable administration of required doses of medication may be particularly important in order to facilitate patient compliance and accurate treatment of the condition. In view of the human involvement, government regulations and industry standards often impose requirements for control of electromagnetic emissions, power leakage, and the like.

Ambulatory insulin infusion pumps have been developed for the administration of medicaments such as insulin for those diagnosed with both type I and type II diabetes. These pumps offer an alternative to multiple daily injections of insulin by an insulin syringe or an insulin pen. They also allow for continuous insulin therapy. In addition, some ambulatory infusion devices can include data collection and storage mechanisms, which allow a diabetic patient/user and/or a caregiver (e.g., doctor, health care worker, family member, and so forth) to easily monitor and adjust insulin intake. The infusion device may be powered by a rechargeable battery that requires periodic recharging.

For safety, the user of a medical infusion device must be isolated from electrical hazards when handling the portable medical device during recharging. A "user" refers to a person who is operating the medical infusion device, and may comprise a patient, diabetic person, caregiver, and the like. Additionally, the user must be isolated from electrical hazards during everyday use. Such use can result in exposure to water and other liquids, e.g., sweat, which may come into contact with the device. When a conventional device becomes wet, the device can malfunction or shut down completely, or might produce an electrical shock to the user of the device. Accordingly, it is also desirable to protect the device in the case that it is exposed to water and liquids, so that the device is still capable of delivering insulin to the patient and maintaining data necessary for operation, while also preventing any bodily harm to the user and/or to the patient. As used herein, the term "user" will be understood to include a person who is a patient, and may include other persons such as caregivers, clinicians, certified diabetes instructors (CDEs), medical professionals, and the like, depending on the context in which "user" is mentioned.

There is a need for a portable device that safely facilitates user interaction, data collection, and recharging while providing electrical and data isolation. In this way, it is not necessary for the portable device to be removed from a patient while connecting the device to a power source or data communications host.

SUMMARY

As disclosed herein, a portable device includes a housing having a front surface and back surface that are spaced apart and enclosed by side surfaces to define an internal cavity, and an electrical connector port that is fitted to the housing and extends into the internal cavity. The electrical connector port receives electrical power and data such that the electrical connector port directs the electrical power to a power isolation connector and directs the data to a data isolation connector. The housing and electrical connector port are configured to provide a seal that prevents the passage of moisture into the internal cavity. In one embodiment, the seal is formed between the electrical connector port and the electrical connector port door with an overmold that prevents the passage of moisture into the internal cavity. The portable device provides electrical and data isolation and also prevents the passage of moisture into the internal cavity.

In other aspects, disclosed herein is a portable medical device which is capable of being coupled to a dedicated power source, e.g., wall outlet, or to a configured power source, e.g., personal computer. The infusion device is further designed such that the connection to either of these sources is available during use of the device. The infusion device is also designed to withstand exposure to water and other liquids, which may otherwise harm the user or alter the functionality of the device.

Other features and advantages of the present invention will be apparent from the following description of the embodiments, which illustrate, by way of example, the principles of the invention.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Disclosed herein are embodiments of an electrically-powered portable device that is periodically recharged and is capable of operation while also being isolated from a host device from which it receives power and with which it exchanges data. The portable device includes components that are physically insulated from outside elements, such as liquids.

The aforementioned isolation features of the portable device are often based on regulations and other requirements to ensure user safety during use of the portable device. Such requirements vary for different portable devices and, in particular, for portable medical devices that provide a more critical function to a patient. For example, isolation from the electrical current provided during charging of the device ensures that the user will not incur an electrical shock during use and details of the isolation are often specified by government regulations or by safety licensing bodies. The isolation from outside elements allows the device to continually function. For example, the isolation ensures that the device will not suffer a short circuit from water damage, ensuring proper insulin delivery to a user and preventing electrical shock to the user. Not only may isolation of certain elements within the device be necessary for regulatory compliance, it also may be important to meet electrical requirements of the device elements. For example, proximity of components to the housing and between other electrical components can cause capacitance issues and voltage hazards for the user. Furthermore, emissions from the various components within the portable device should be controlled to minimal levels to be within a safe operating range for a patient. Various regulatory standards are further discussed in the following description of the portable medical device of the present invention.

Figure 1:
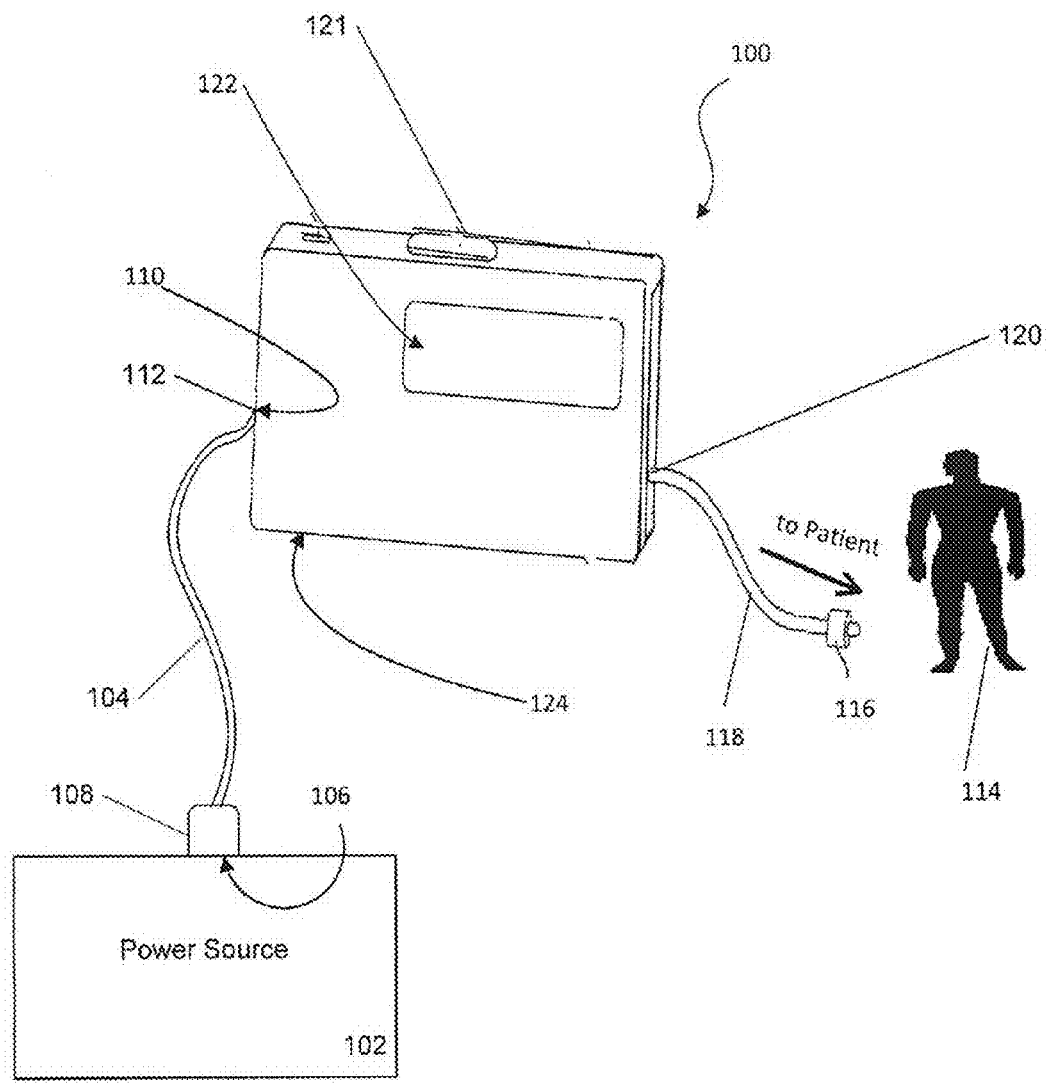
FIG. 1 depicts a portable device according to an embodiment of the present invention that is coupled to a host device and is electrically isolated from the host.

FIG. 1 shows an electrically-powered portable device 100 that is coupled to a host power source 102, such as a desktop or laptop computer, through a cable 104. The cable may comprise, for example, a coupling through which both data and electrical energy are received at the portable device 100. Examples of such combined power and data cables include a Universal Serial Bus (USB) connection, an IEEE 1499 connection, a "THUNDERBOLT" connection (i.e., from Apple, Inc, of Cupertino, Calif., USA), PCI Express, eSATA and Ethernet. The host power source 102 is a source of electrical energy and can be any type of computing device that includes a port 106 that receives a connector 108 of the cable 104. The port of the host computing device may comprise, for example, a USB port, or IEEE 1499 port, or port for THUNDERBOLT, PCI Express, eSATA or Ethernet. A compatible connector port 110 of the portable device 100 is coupled to the cable 104 at an opposite end 112 of the cable. In a USB implementation, for example, the cable 104 is a USB cable and associated connections and ports may support one or more of USB version 1.1, 2.0, or 3.0 data transfer speeds.

The portable device 100 may be coupled to a patient 114 via an infusion port 116 and a connecting tube or cannula 118. The connecting tube is coupled to the portable device 100 at a fluid dispensing port 120. The portable device may include control features, such as buttons or switches 121 to receive user input and control pumping and the like, and may include a display screen 122 on which messages and alerts are displayed. The display 122 may comprise, for example, a touch-screen on which user inputs may be received. A housing 124 of the portable device encloses internal components, such as fluid reservoirs, electrical components, battery, and the like. The portable device 100 illustrated in FIG. 1 comprises a portable medical device of the type worn by a patient 114 such that insulin or other fluid is delivered via the connecting tube 118 and the fluid dispensing port 120. Exemplary ambulatory medical devices and features include those, e.g., disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495. Each of the aforementioned documents is hereby incorporated herein by reference in its entirety.

With such combined power and data connections, data may be exchanged between the portable medical device 100 and the host power source 102 over the cable 104, and the portable device 100 may also receive electrical power from the host power source over the cable. As described further below, the portable device 100 incorporates an electrical isolation feature in which the circuitry within the portable device for both data and power is electrically isolated from the power source 102. Additionally, the electrical isolation feature within the portable device 100 allows for circuitry within the device to be protected from outside elements, with which the device may come into contact with during normal every day operation. The operation of the portable device is also controlled so as to reduce radio frequency (RF) emissions. In all of the aforementioned embodiments, because of the isolation feature of the portable device 100, the connection of the portable device to a patient 114 may be maintained even as the device is connected and disconnected from the source computer 102, and even as the device is exposed to liquids, such as water, without fear of electrical shock or undue RF emissions to the patient 114.

The portable medical device 100 of FIG. 1 is designed to operate such that radio frequency (RF) and electromagnetic field (EMF) emissions from the portable device are maintained at safe levels for close human interaction throughout operation of the device, including operating states such as a charging state, power up state, inactive state, e.g., shelf or suspend mode, and active state, such as when all components fully functional. EMF emissions from portable devices are regulated to require such emissions to be within specified levels in order to be considered acceptably safe.

Those skilled in the art will understand that a combined data/power connection such as USB, IEEE 1499, THUNDERBOLT, PCI Express, eSATA, and the like must be configured for power delivery before full utilization for recharging of the connected portable device is possible. That is, upon initial coupling of a portable device to a combined data/power connection of a host computer device, only a reduced current flow is available. After communication between the device and the host computer through a connection port has been completed and the connection has been properly configured, then a greater amount of current is available to the device that is sufficient for device operation as well as battery recharging. In further embodiments, the power cable connector 104 may be connected to a power source 102 that is a dedicated power supply (without data exchange capabilities) connected to a source such as a conventional wall outlet, car power outlet (e.g., cigarette lighter connection), or other power-only source. For example, the power source 102 may comprise a power converter that receives a line AC voltage and produces a DC output voltage at a predetermined voltage level. The aforementioned type of power supply will be referred to herein as a dedicated power source or dedicated power supply. In the case of a dedicated power source, no configuration is necessary to draw full recharging power from the power source, and the available source current is not dependent on configuration, i.e., the dedicated power source is considered a high voltage source upon connection to the portable device 100.

Figure 2:
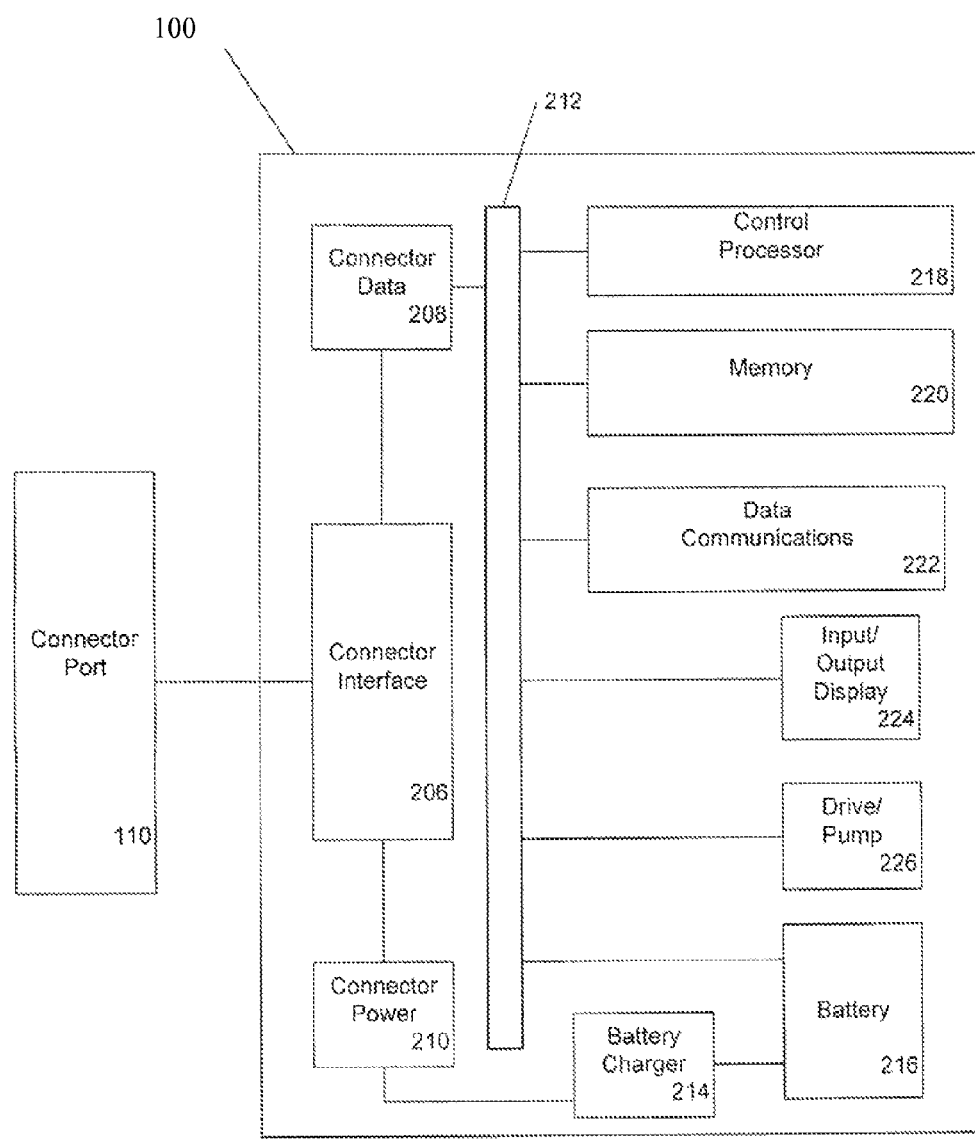
FIG. 2 is a block diagram of circuitry and components for a portable medical device embodiment with electrical power isolation and data isolation.

FIG. 2 shows a block diagram of the components within the portable device 100 of FIG. 1. The portable device 100 includes a power management system that is connected to the connector port 110 that receives a combined data/power cable, such as the USB cable 104 illustrated in FIG. 1. That is, the cable 104 has the capability of simultaneously providing electrical energy for charging and data transmission for communications. A connector interface 206 supports data exchange and receives electrical power through the connector port 110, and controls a connector data element 208 and a connector power element 210. The device may be powered by battery power in place of or in addition to the connector interface. The connector interface 206 passes data communications from the connector port 110 through the connector data element 208 to a system bus 212. The connector interface 206 passes electrical power from the connector port 110 through the connector power element 210 to a battery charger 214, which in turn is coupled to a battery 216 and which recharges the battery 216. In one embodiment, the connector data element 208 is implemented in the FIG. 2 device with a USB Isolation Chip ADUM4160 product from Analog Devices, Inc. of Norwood, Mass., USA, and the connector power element 210 is implemented in the FIG. 2 device with a USB Power Isolation Chip LT3573 product from Linear Technology Corporation of Milpitas, Calif., USA. Those skilled in the art will be aware of alternative suitable devices.

A control processor 218 is connected to the system bus 212 and receives the data communications from the connector data element 208 for processing. The control processor controls operation of the various elements of the portable device 100 that are connected to the system bus 212. The control processor operates according to program instructions that may be stored in device memory 220. Program instructions may be stored in processor memory incorporated in the control processor 218. The control processor also stores data from its operations in the device memory 220. The control processor 218 controls a data communications element 222 that may comprise a receiver/transmitter for wireless RF communications, such as "WiFi" communications or "Bluetooth" communications between the portable device 100 and compatible external systems and networks. The device 100 includes an output/display element 224 such as a touchscreen display, operating buttons or switches, and the like. The device 100 of FIG. 1 comprises an infusion pump device, and therefore also includes a drive/pump element 226 such as a pumping mechanism for delivery of fluid such as insulin to the connecting tube 118, as described above in connection with FIG. 1. To meet industry standards and governmental regulations, the connector data element 208 and the connector power element 210 are both electrically isolated from the other device components, so as to provide a device that can be safely connected to the power source and the patient at the same time.

The memory 220 of the device 100 may be any type of memory capable of storing data and retrieving that data for transfer to one or more other components of the device, such as the control processor 218. The memory may comprise one or more of a Flash memory, SRAM, ROM, DRAM, RAM, EPROM or dynamic storage. For the illustrated portable fluid delivery device 100 of FIG. 1, the device memory 220 may be coupled to the control processor 218 and may be configured to receive and store input data and/or store one or more template or predetermined fluid delivery patterns. For example, the memory can be configured to store one or more personalized (e.g., user defined) delivery profiles, such as a profile based on a user's selection and/or grouping of various input factors; past generated delivery profiles; recommended delivery profiles; one or more traditional delivery profiles, e.g., square wave, dual square wave, basal and bolus rate profiles; and/or the like. The memory can also store user information, history of use, glucose measurements, compliance, an accessible calendar of events, and the like. In some embodiments, the memory 220 of the portable medical device 100 may have a data capacity of up to about 10 GB, more specifically, up to about 3 GB, even more specifically, about 1 MB to about 200 MB. In some embodiments, the memory of the infusion device 100 may be up to about 3 GB, more specifically, up to about 500 MB, and even more specifically, about 200 kB to about 200 MB.

Figure 3:
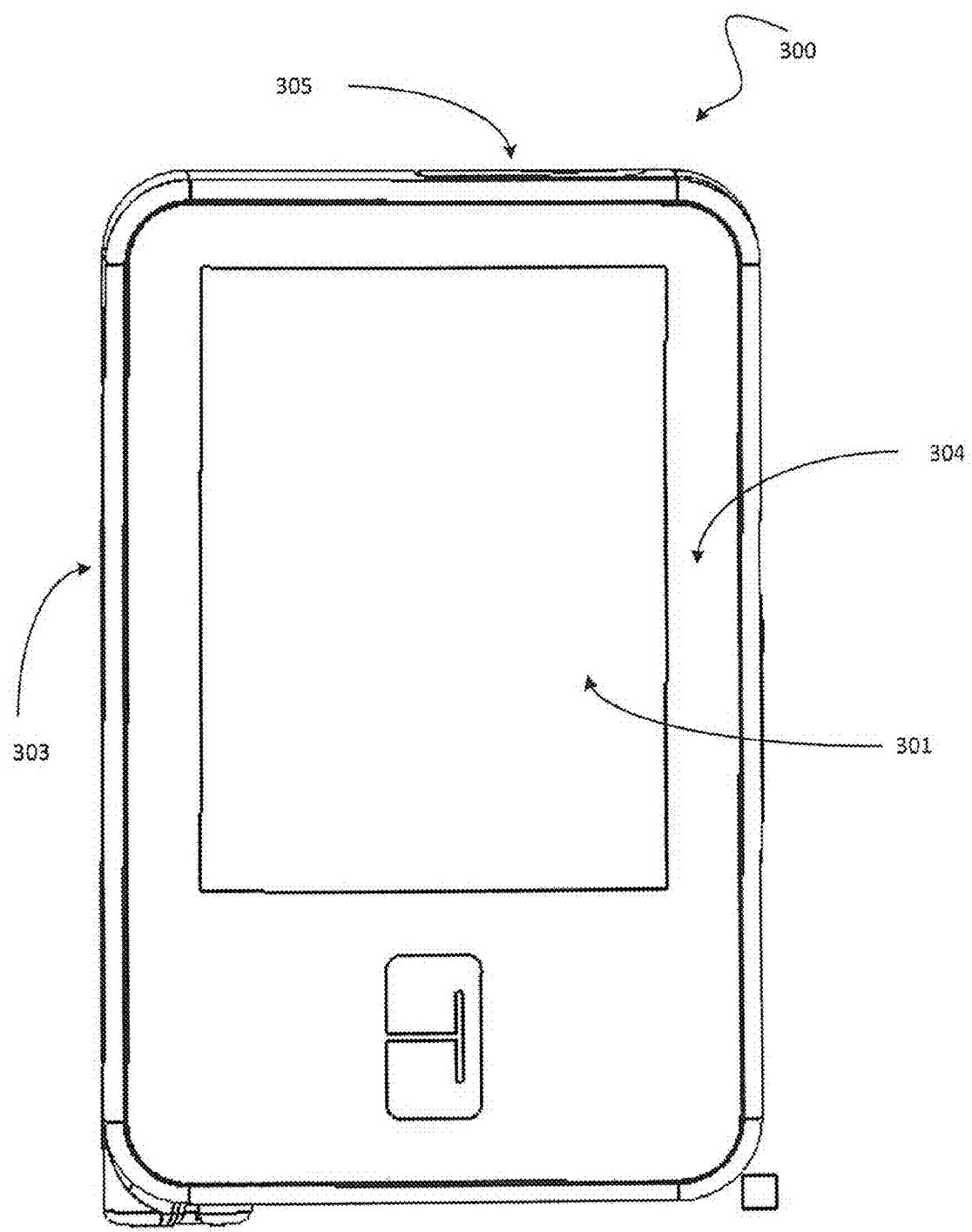
FIG. 3 is a schematic that depicts the front side of a portable medical device in an embodiment.

FIG. 3 shows a front view of a schematic of a portable medical device 300, such as the portable device illustrated in FIG. 1, configured as an infusion pump for delivery of insulin to patients with diabetes. As shown, the device includes a housing 303 having a front face 304. The front face 304 includes an output display element 301, such as a touchscreen capable of responding to user interaction "touches" as inputs to control the functionality of the device. The touchscreen 301 can occupy sufficient surface area of the front face 304 of the device to facilitate convenient user interaction with the device.

The portable medical device 300 includes a housing 303 that can be of any suitable shape and size to house the device components. For example, the housing 303 may be extended and tubular, or in the shape of a square, rectangle, circle, cylinder, or the like. The housing may be dimensioned so as to be comfortably associated with a user and/or hidden from view, for example, the housing may be sized to fit within or beneath the clothes of a user patient. In some embodiments, the housing 303 of the portable medical device may have a width of about 2 inches to about 5 inches, a height of about 1 inch to about 3 inches, and a thickness of about 0.25 inch to about 0.75 inch. More specifically, the housing 303 may have a width of about 2.5 inches to about 3.5 inches, a height of about 1.5 inches to about 2.5 inches, and a thickness of about 0.4 inches to about 0.8 inches. For some embodiments, the housing 303 of the infusion device 300 may have a width of about 2.5 inches to about 3.5 inches, a height of about 1 inch to about 2 inches and a thickness of about 0.2 inches to about 0.6 inches. The materials of the housing may vary as well. In some embodiments, the housing 303 may comprise a watertight, metal housing that may be opened and disassembled for repairs. In some embodiments, the housing may be a watertight, plastic housing.

As shown in FIG. 3, a door 305 can be located on one side of the device 300. The door 305 can provide a cover to protect an interface, e.g., an electrical connector port interface, to which the device can receive a charger. The door 305 can be located on any side of the device, dependent on the internal configuration of the components. In some embodiments, the door 305 can extend from a first side of the portable medical device housing to a second side of the housing.

Figure 4:
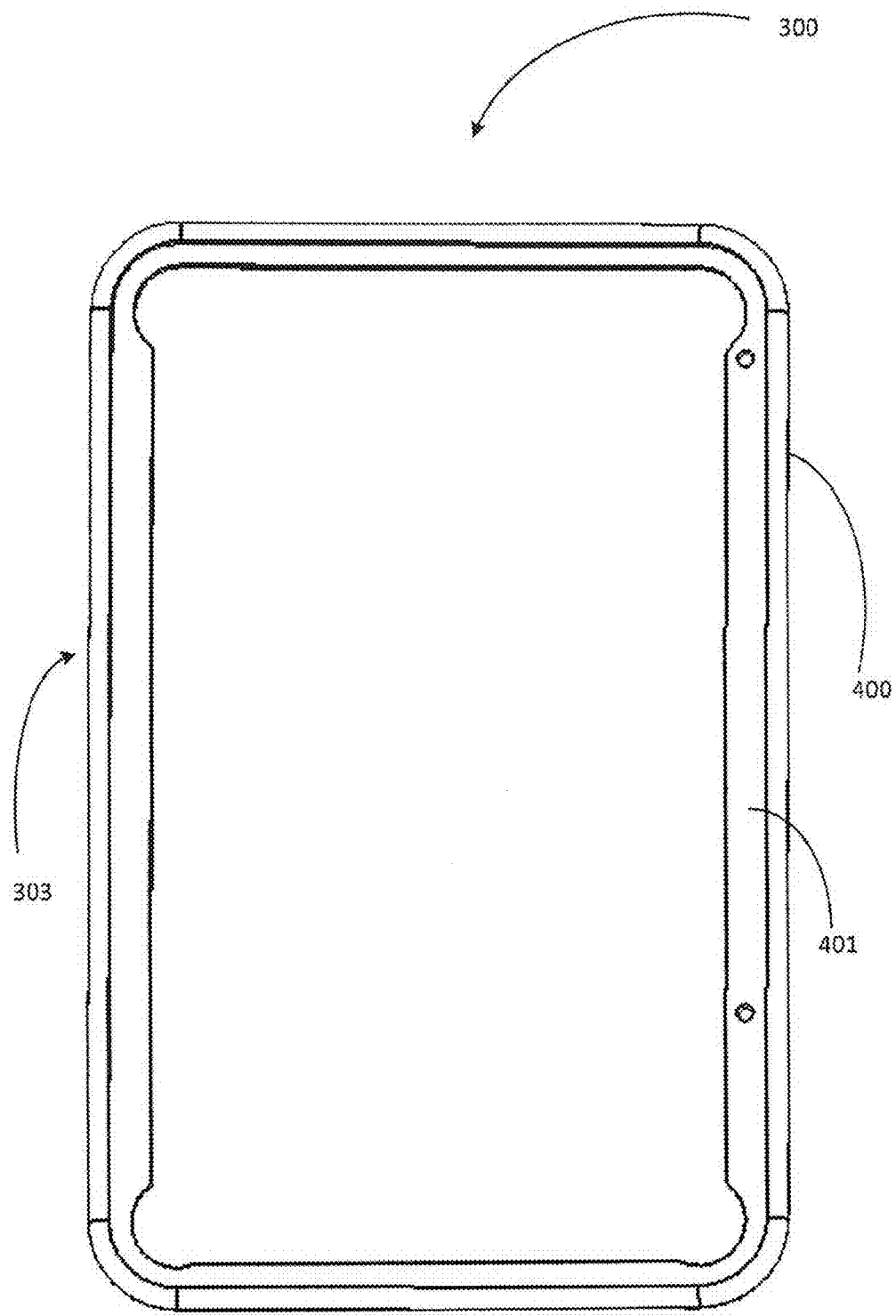
FIG. 4 is a schematic that depicts the circuitry and components of a portable medical device with the front side housing removed as in FIG. 3.

FIG. 4 illustrates a view of the housing 303 along the outer edges of the portable medical device 300, including an outer shell 400 and an inner shell 401. The outer shell 400 can be metal, hard plastic, carbon fiber or another material utilized to externally protect the device from environmental damages. The inner shell 401 can be utilized to form a seal along the outer shell 400, such that liquids cannot enter the portable medical device and harm any of the internal components. The inner shell 401 can be a rubber, plastic or other polymer material capable of forming an impermeable seal under pressure.

Figure 5:
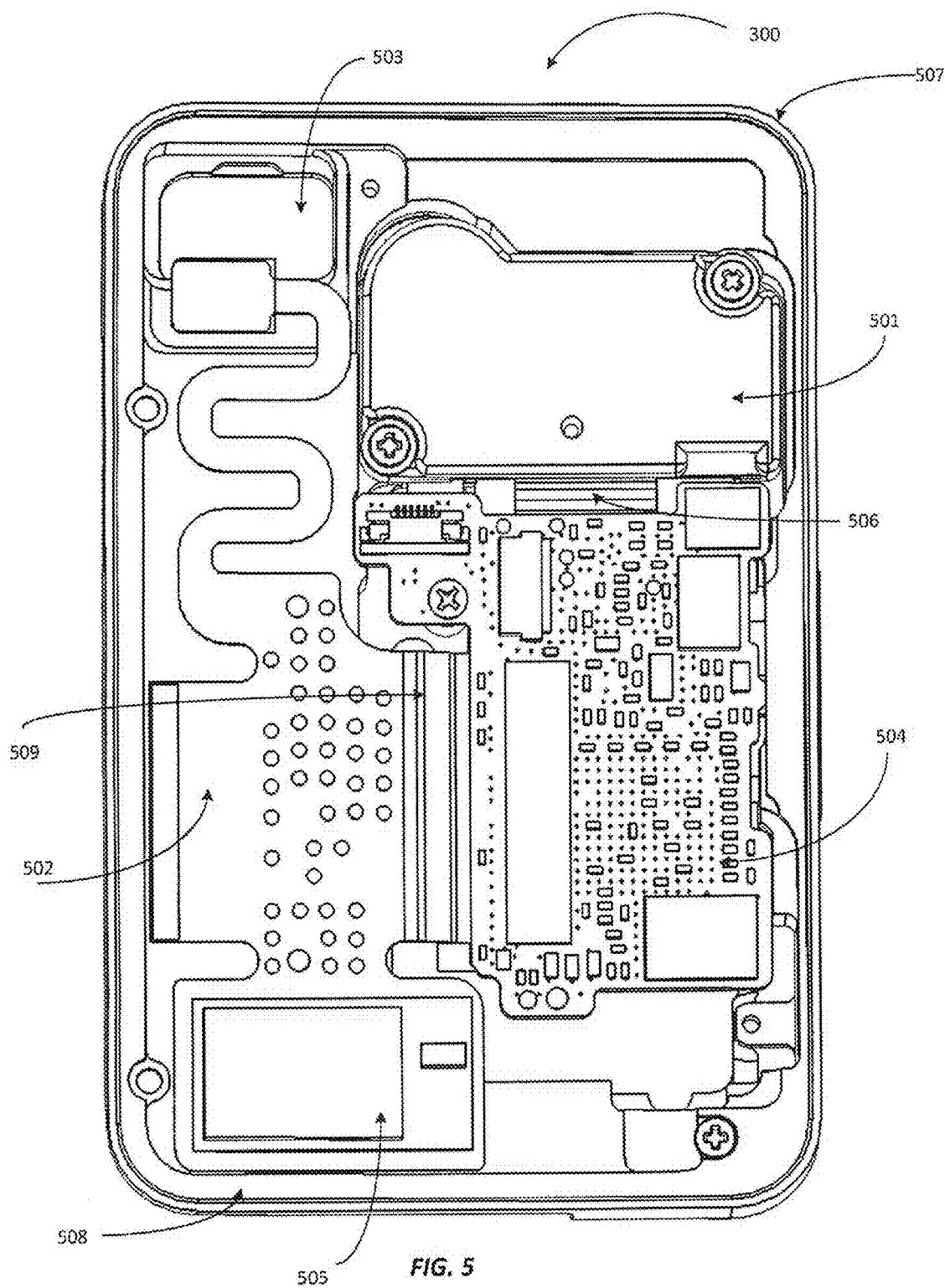
FIG. 5 is a schematic that depicts the circuitry and components of a portable medical device with the front side housing removed as in FIG. 3.

FIG. 5 provides a schematic representation of FIG. 3 with the front face of the housing removed and the internal components exposed. As shown, the portable medical device 300 can include a printed circuit board (PCB) assembly including a flex serpentine board 502, a main board 504, a connector for the flex board and main board to direct current (DC) 506, a pressure board 503, and a connector for the flex board to the pressure board 509. Additionally, the device includes a Bluetooth PCB assembly 505 for short wave, such as radio frequency (RF) communication. Such communication can be useful if a user of the device wishes to transfer data to, for example, a Bluetooth-enabled mobile telephone, such as a Smart Phone.

FIG. 5 shows that the portable medical device 300 also includes an overmold 501, which thermally and physically separates the PCB assembly from the connector port interface, utilized for charging the device. The internal components of the device are all separated from the outer shell 507 of the housing in order to prevent any interaction between the internal components and the housing during use of the device, such as when the device may be bumped or jostled by the user. The internal components can be separated by the distance of at least the inner bezel 508, described with reference to FIG. 4. The internal components can additionally reside in a cavity created by the outer shell 507, such that the components do not interact with the front face of the device, when assembled.

As previously mentioned, within the housing 303, certain physical design requirements may also exist which are based on, e.g., regulatory requirements. For example, the portable medical device 300 may have include restrictions imposed on the spacing between other components in the portable medical device and/or the housing 303 in order to properly insulate each printed circuit board (PCB) trace as well as the components and the housing of the device, which can be made of a conductive material. When certain components are too close to one another within the device, phenomena such as voltage creepage can occur between each conductor. Such spacing requirements can influence the design of the portable medical device, due to the size and number of the components within the device as well as the voltage drop of those components within the device.

In further embodiments, the portable medical device 300 includes isolation and emission control features. Additionally, the device includes a defined architecture for how electrical power is delivered to various components of the portable medical device. In one embodiment, the power is supplied through the electrical connector port interface (shown in FIGS. 10-11), which supplies 4.65 volts (V) and draws a minimum of 100 mA and a maximum of 500 mA of current, depending on the power source and configuration of the connection interface. The power is supplied to a, for example, USB data-isolation integrated circuit (IC) chip 1102 (not illustrated in FIG. 5; see 1102 shown in FIG. 11) and a USB power isolation IC chip. The power isolation chip resides below the overlay 501, which insulates the electrical current from a user of the device during charging and/or data transfer. Each chip is capable of receiving the maximum power provided when the device is connected to a power supply source. The data isolation chip 1102 draws more current than the power isolation chip and includes a quiescent current that reduces the charge current of the low mode charging (also referred to as shelf mode or suspend mode) for the battery (not shown). The battery is charged by a battery charger IC chip that checks the battery charge level when the portable medical device detects that it is connected to a power source. The output voltage from the USB power isolation chip is coupled to the battery charger chip to supply electrical charge to the battery. The output of the battery charger chip, when the infusion device is connected to a USB power supply source, is coupled to a fuel gauge (not shown), which determines the current battery charge. The output of the battery charger is also supplied to the fuel gauge. The fuel gauge is useful in the case that the portable medical device is not connected to a USB power source, so that no power flows through the battery charger chip, because the fuel gauge permits the battery charge to be known to the system so it may determine which components should be supplied power during startup.

As noted in connection with FIG. 2, control of the device is provided from a control processor. The control processor may be provided as a two-element processor, comprising a data control processor and a power control processor, each part of the main PCB 504. To meet industry standards and government regulations, the data isolation chip 1102 and the power isolation chip provide isolation from the other device components so that the chips reduce EMF emissions and provide a safely functioning device that can be connected to the power supply source and the patient at the same time. For example, the data isolation chip 1102 is implemented in the FIG. 5 device with a USB Isolation Chip ADUM4160 product from Analog Devices, Inc. of Norwood, Mass., USA, and the power isolation chip is implemented in the FIG. 5 device with a USB Power Isolation Chip LT3573 product from Linear Technology Corporation of Milpitas, Calif., USA. Those skilled in the art will be aware of alternative suitable devices to provide the data and power charging functions with isolation.

Figure 6:
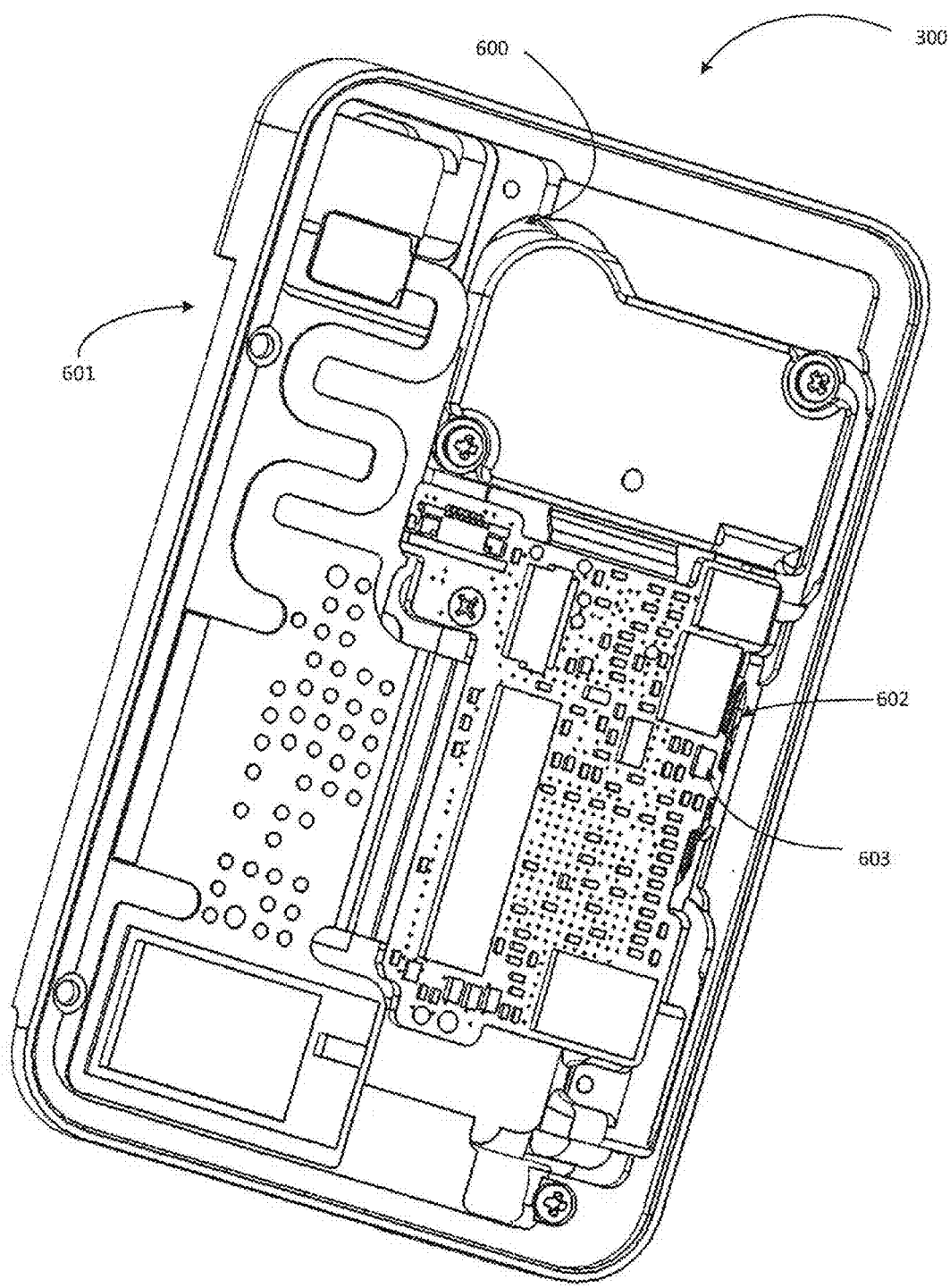
FIG. 6 is a perspective view of FIG. 5 in which the cartridge side of the portable medical device is shown in one embodiment.

Referring to FIG. 6, a perspective view of the portable medical device 300 in FIG. 3 and FIG. 4 is illustrated in an embodiment. The portable medical device with electrical power isolation and data isolation includes a slot 601 for receiving a replaceable medicament cartridge for, e.g., insulin. The cartridge slot can be located proximate to one side wall of the device housing such that the cartridge accessibility and removal is facilitated. The portable medical device can include an input button 602 including an outer shell 603 (shown in FIGS. 16A and 16B).

Figure 7:
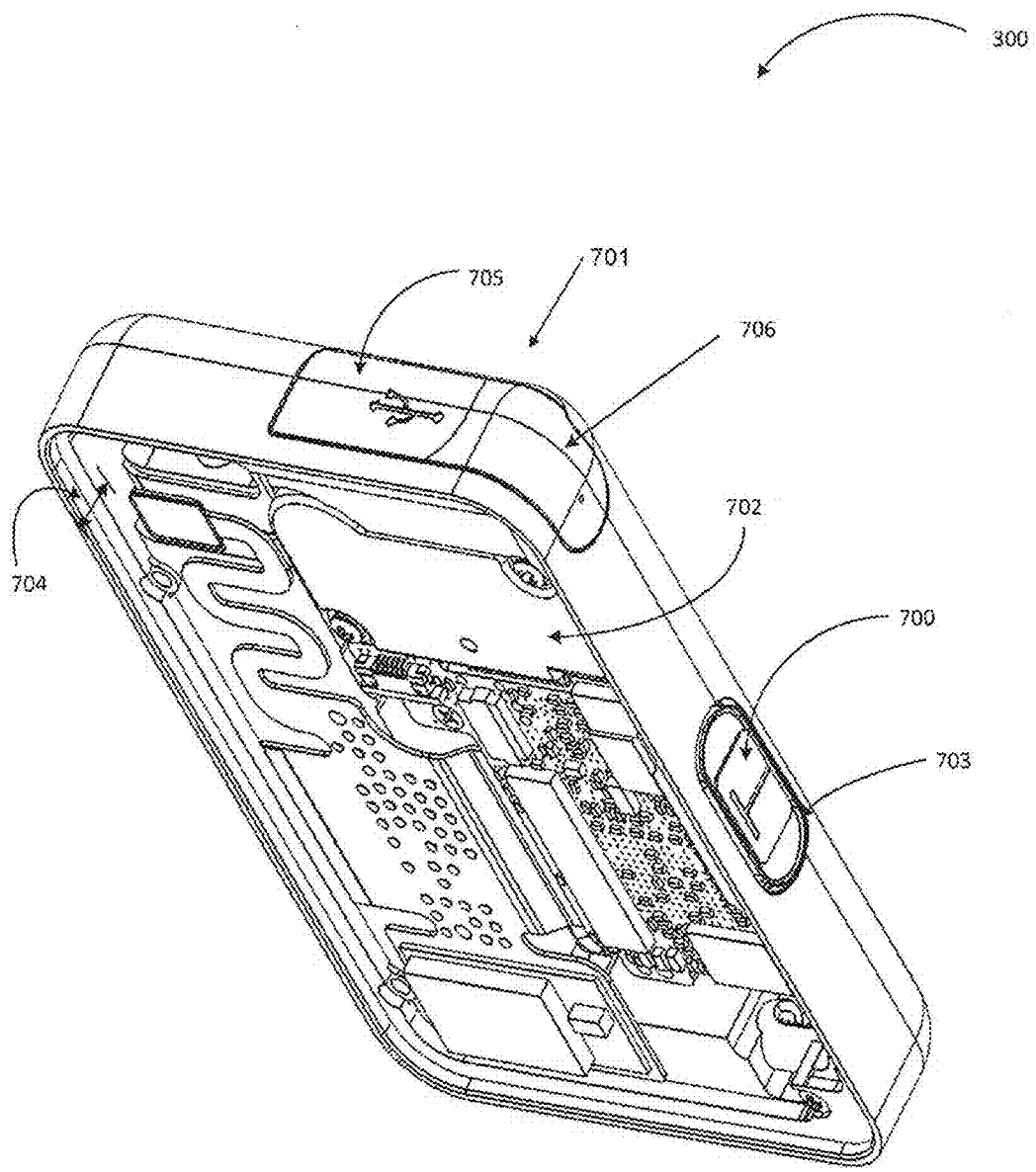
FIG. 7 is a perspective view of FIG. 5 in which a top and side of the portable medical device are shown in one embodiment.

FIG. 7 is an alternative perspective view of the portable medical device 300 in one embodiment. As shown, one side wall of the device housing includes an electrical connector port door 701. The electrical connector port door 701 includes two parts: a plug bezel 705 and a flexible joint 706. The flexible joint 706 includes a plug 1104 (shown in FIG. 11) that is utilized to affix the door 701 to the portable medical device 300. The plug bezel is a movable portion of the electrical connector port door 701, which is removed each time that the USB port is utilized. The electrical connector port door 701 can be made of a rubber or soft polymer, which is capable of bending, flexing, and maintaining shape without breaking from continual use. As shown in FIG. 7, the electrical connector port door 701 is in a closed position.

The device 300 also includes an input button 700 on one side wall of the housing of the device, which differs from that of the electrical connector port. The input button 700 can be any suitable size or shape that can facilitate providing user input to the device. In some embodiments, the input button 700 can be utilized to wake the device from a sleep mode, lock the touchscreen of the device, and power-off the device. The button 700 can be made of any material that is capable of withstanding repeated user interaction, such as a metal, plastic or polymer, or rubber. In order to further facilitate user interaction with the input button 700, the button can include a bezel 703, which is illuminated during usage of the button. The input button is further described in the following paragraphs with reference to FIGS. 16A-C.

Still referring to FIG. 7, the cavity created by the housing of the device is shown as the distance 704 from the top of the housing wall to the components within the device. As previously mentioned, this allows for additional protection of the internal components from contacting the front face of the device during usage.

Figure 8:
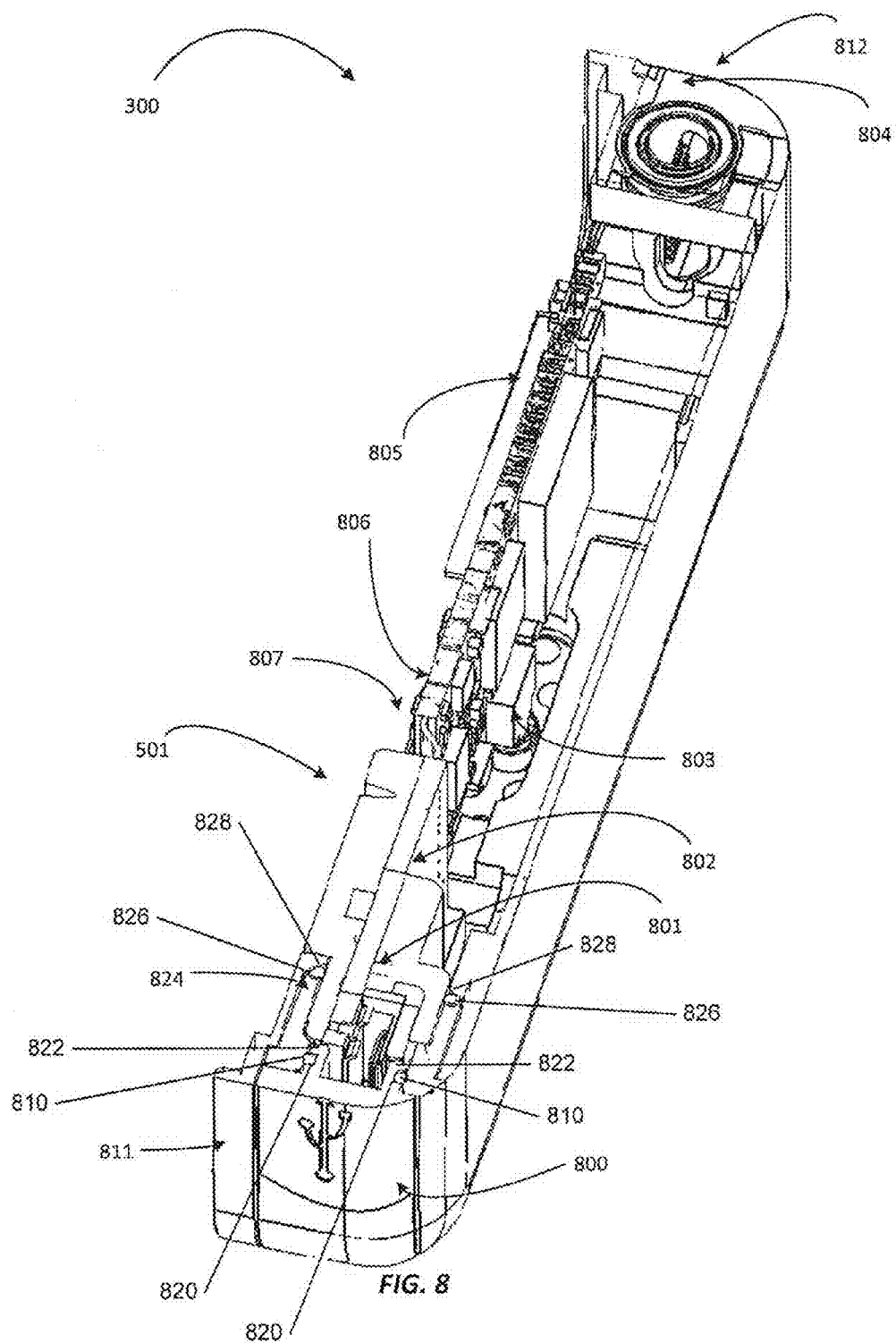
FIG. 8 is a schematic that depicts a cross-sectional view of the portable medical device in FIG. 5.

FIG. 8 depicts a cross-sectional perspective view of the portable medical device 300. The electrical connector port, such as a USB port 801, is shown with the electrical connector port door 800 in a closed position. As shown, the electrical connector port door 800 is held in place via an o-ring 810, which itself is held within grooves 820 of door tabs 822. The door 800 is inserted into the housing against a door bezel 824, against which the o-ring 810 is compressed and forms a seal. The seal of the o-ring 810 aids in preventing outside elements and debris from entering into the device through the internal cavity of the electrical port. Additionally, the o-ring can aid in securing the door 800 closed. The o-ring 810 is described in further detail below with reference to FIG. 10. Also shown in FIG. 8 is a primary o-ring 826, which provides another seal against the entry of outside elements and the like.

FIG. 8 depicts that the overmold 501 previously described with reference to FIG. 5 includes an upper portion 807 and a lower portion 802 that are connected together and wrap around the PCB sides. The overmold portions 807, 802 can vary in thickness along the surface of the USB interface in order to accommodate various internal components residing below, such as a DC-to-DC PCB, electrical connector port 801, transformer (not shown in FIG. 8), and power isolation chip (not shown in FIG. 8). The DC-to-DC PCB can be flexibly coupled to the main PCB 805 by a flexible PCB 806, which is also illustrated in FIG. 5. As previously discussed, the internal components can reside in a cavity formed by the outer shell 811 of the housing. The housing can also include an inner shell, which can be compressed to form a seal preventing water ingress to the portable medical device.

FIG. 8 also depicts that a crush seal occurs with the interaction of the bezel 809 pushing the primary o-ring 826 against an angled sealing surface 828 on the housing. This interaction compresses or crushes the o-ring into the overmold, creating a seal at the interface of the bezel, the enclosure, and the overmold. Sealing due to the overmolding process creates a barrier such that moisture can't penetrate past the discrete connector on the board (i.e., the micro-USB connector). Therefore, no leakage can occur through the micro-USB or passed the interface of the overmold around it, creating the sealed connector port.

Referring still to FIG. 8, the input mechanism 803, forming a connection between the input button (shown in FIG. 7) and the main PCB 805 is shown. The input button, input mechanism, and surrounding components are further described with reference to FIGS. 16A-C in the following paragraphs. The cross-sectional view in FIG. 8 also shows a rack pushrod 804, which forms the actuator driving the insulin delivery from the insulin cartridge. The rack pushrod 804 can be encapsulated by a cover 812 made of flexible material, such as a rubber or soft polymer, which forms a barrier between the cartridge and the rack mechanism. The pushrod cover 812 can form a barrier, or seal, between the internal components of the portable medical device, e.g., through the rack mechanism, and the cartridge in case any accidental leakage occurs within the cartridge.

Figure 9:
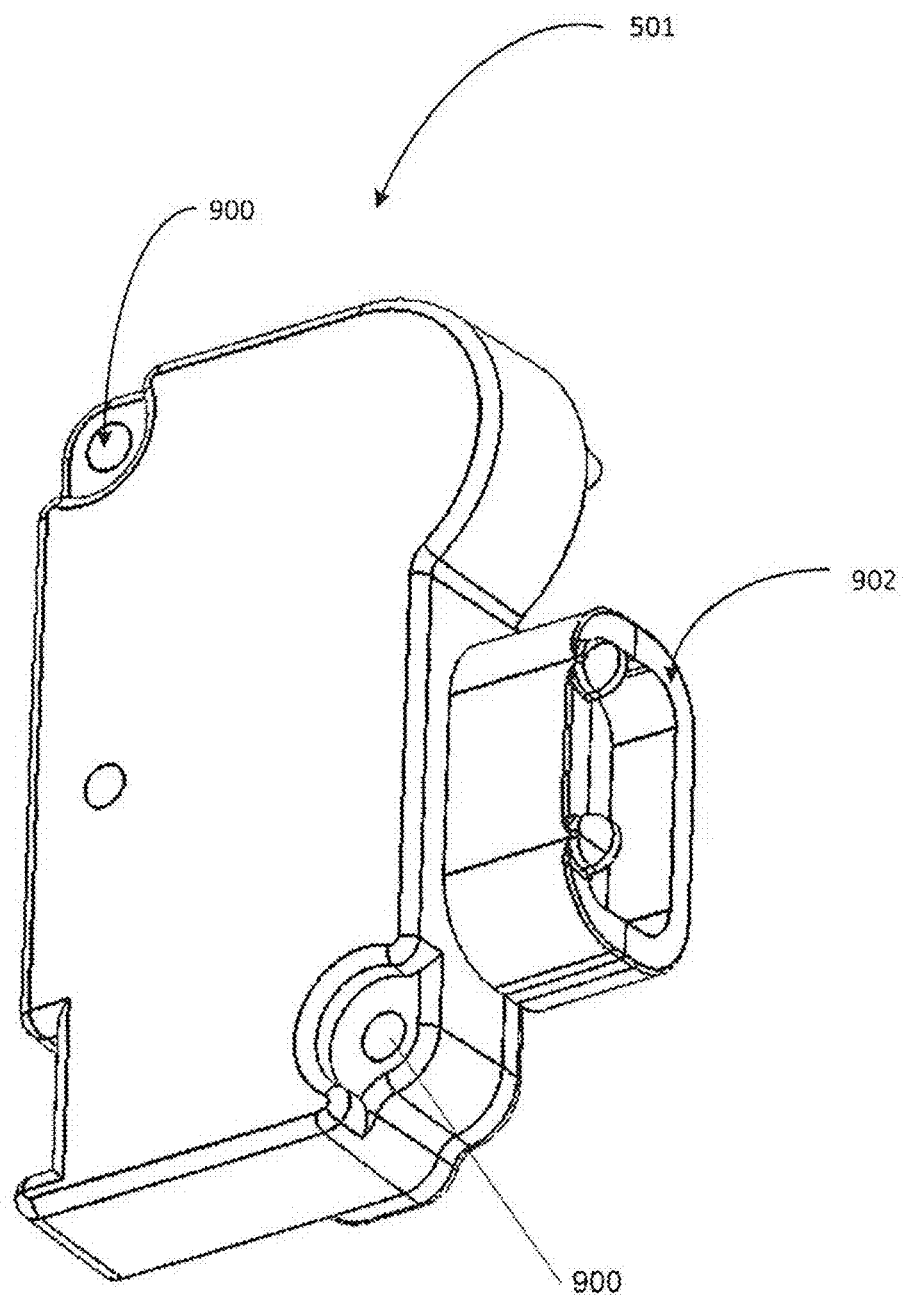
FIG. 9 is a schematic that depicts a top perspective view of an electrical connector port assembly used in the portable medical device of FIG. 3 in one embodiment.

FIG. 9 is a schematic representation of the overmold 501 and electrical connector port 902 assembly. The overmold 501 may be shaped according to the power isolation chip and associated circuitry in order to meet regulatory requirements for a medical device to prevent any harm incurred by a user of the portable medical device and prevent any liquid from contacting the electrical connector input elements of the device. The overmold 501 may be made of an insulator material, which aids in preventing voltage creepage and emissions from the internal components of the device. The overmold may be made of a plastic polymer, dielectric, or other non-conductive material that is capable of being pre-formed and can maintain its shape during use. The overmold can be pliable under certain conditions, such as extreme temperatures in order for molding into the preformed shape to occur. In some embodiments, the overmold may be a membrane formed on the components. The overmold 501 is also capable of maintaining shape and protecting the components over which it is assembled during temperature changes, e.g., due to dissipation from the circuits. The overmold can be secured to the PCB board and other internal device components utilizing screw fasteners, such as screws (not illustrated) that are threaded into two screw holes 900. The screw holes may be positioned on the overmold as needed to ensure a seal. The screw holes 900 guide the screws to pass through the PCB and into corresponding threaded holes in the housing. In this way, the screws are electrically isolated from the PCB. The electrical connector port mouth 902 can be formed with the overmold 501 or as a separate component from the overmold. The electrical connector port mouth 902 can be made of a similar non-conductive material as the overmold that is capable of forming a barrier around the electrical connector port and capable of securely receiving a electrical connector plug during charging and data transfer.

Figure 10:
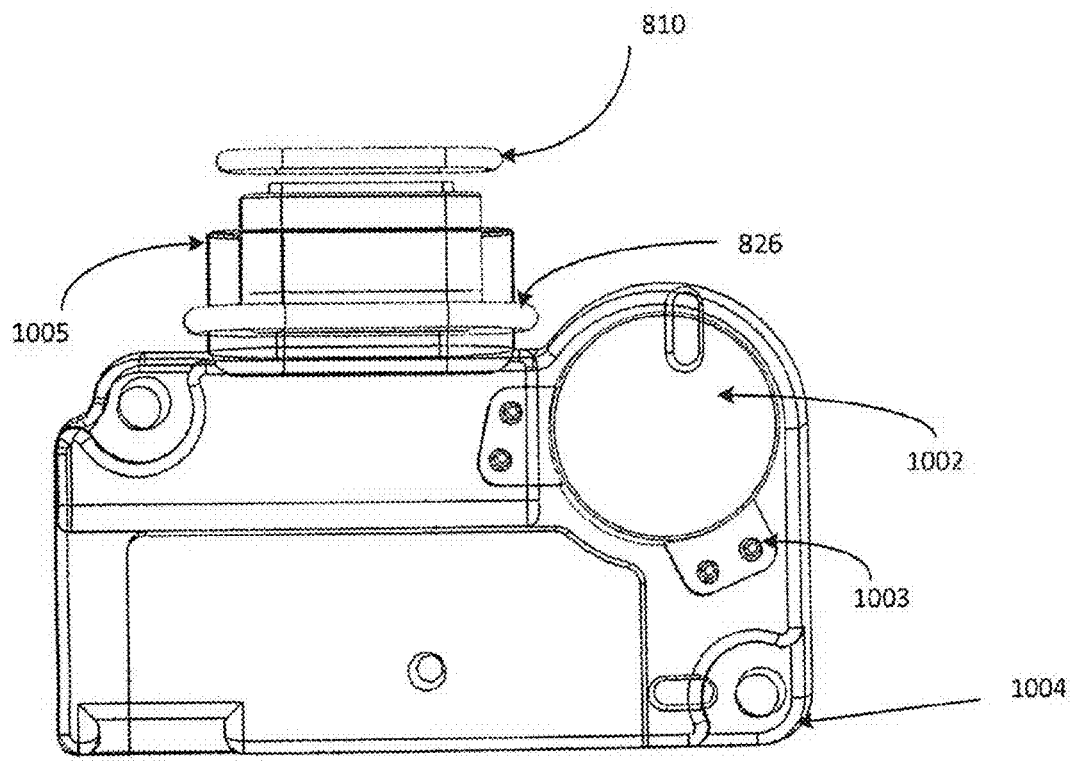
FIG. 10 is a schematic that depicts a bottom view of the electrical connector port assembly of FIG. 9.

FIG. 10 is a schematic representation of the electrical connector port and power isolation assembly from a bottom view perspective. The power isolation assembly includes the electrical connector port mouth 1005 and the two o-rings 810, 826 described above in connection with FIG. 8. The o-ring 810 helps secure the placement of the door within the housing of the portable medical device and along with the primary o-ring 826 helps to prevent any outside environmental elements, such as liquids, from entering the device. The first o-ring 810 can provide a lip onto which an electrical connector port door (not shown) can securely hinge while in a closed position. FIG. 10 also illustrates the overmold 1004, which is formed over the entire power isolation assembly to prevent any possible electrical shock to a user of the device and to lower radiation emissions and heat dissipation from the device during charging. As previously mentioned, the overmold 1004 can be made of a non-conductive material, such as a plastic polymer, which is capable of absorbing heat and voltage.

The power isolation assembly can additionally include a transformer 1002, which controls the electrical input from the electrical connector. The transformer 1002 can be customized to maintain a specified output while receiving variable input currents from the electrical connector, dependent on the compatibility of the power supply utilized to charge the device. Accordingly, the transformer 1002 can have a customized coil turns ratio in the toroid core, such as approximately 1.33:1, or 12:9, to provide a more efficient output for the variable input current. The coil windings can additionally be insulated in order to lower emissions to meet UL or IEC 60601-1 regulatory standards requirements. In some embodiments, the windings are double or triple insulated. The transformer 1002 can include a housing having input leads and output leads, or pins coupled to the coil wires 1003 utilized to the secure placement of the transformer 1002 on the PCB and in order to supply a controlled output to various power isolation assembly components.

Figure 11:
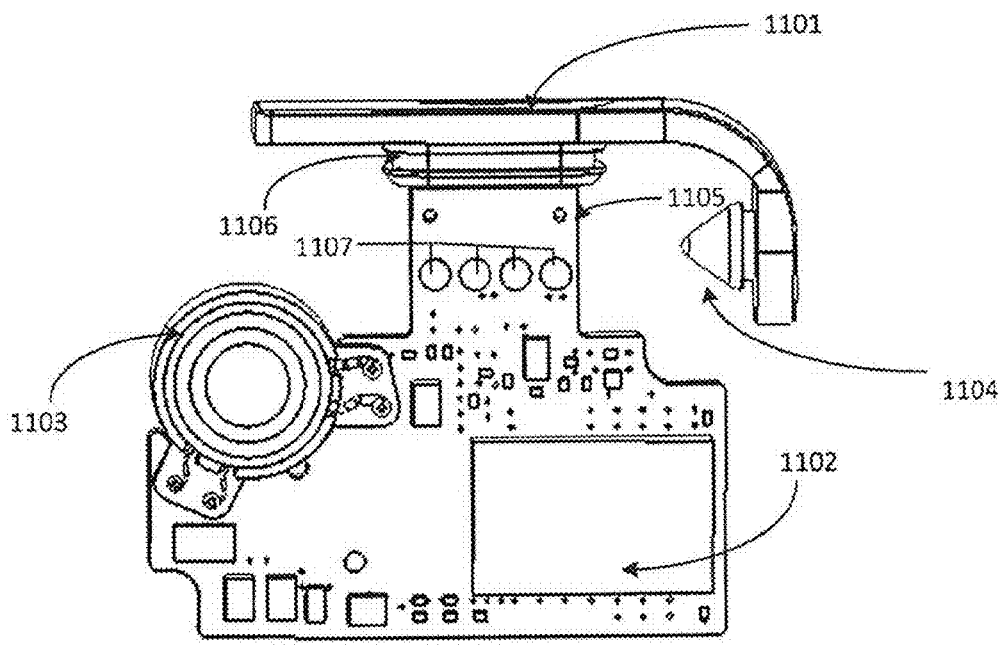
FIG. 11 is a schematic that depicts the electrical connector port assembly in FIG. 10 having the overmold removed.

FIG. 11 illustrates a schematic view of the electrical connector interface including the power isolation circuit, which controls the incoming current and supplies the power to the other components within the device. As illustrated in FIG. 11, a power supply can include four output lines that provide power and supply data from the connector interface with four input points 1107 (shown in FIG. 12) to a data isolation chip 1102 and a power isolation chip (not shown). Similarly to the previously described embodiments, the data isolation chip may be implemented in the portable medical device with a USB Isolation Chip ADUM4160 product from Analog Devices, Inc. of Norwood, Mass., USA, and the power isolation chip may be implemented with a USB Power Isolation Chip LT3573 product from Linear Technology Corporation of Milpitas, Calif., USA. Those skilled in the art will be aware of alternative suitable devices to provide the data and power charging functions with isolation.

A common mode choke can be coupled to the power supply to lower RF and EMF emissions and to limit high frequency noise on the data signal supplied from the power supply. The power supply voltage output and ground lines are fed into two ferrite beads, which behave similarly to the common mode choke, to attenuate high frequency noise signals emitted from the device during use (e.g., during charging/connected operation), while supplying low levels of thermal dissipation and lowering emissions to meet regulatory performance standards. A first ferrite bead provides a voltage output from the power supply directly to the power isolation chip and an isolating device, e.g., a transformer 1103. A flyback switch of the power isolation chip provides the secondary input to the transformer 1103 in order to control the switched modes (e.g., charging and not charging states) of the infusion device.

The schematic view of FIG. 11 shows the electrical connector interface without the overmold. The electrical connector port opening is protected by the electrical connector port door 1101, which includes a door plug 1104 that allows the door to remain fixed to the device during removal and placement over the electrical connector port. The electrical connector door 1101 also includes a door insert 1106, which partially fills the electrical connector port cavity. The door insert 1106, with the o-ring grooves 820, can form a pressurized seal around the cavity of the electrical connector port. The electrical connector port door 1101 can be made from a flexible material, such as rubber or soft polymer, so that repeated removal and placement within the device do not cause breakage.

Referring still to FIG. 11, a USB DC-to-DC board 1105 is also shown. The incoming current from the USB interface is controlled by a customized transformer 1103. The design of the transformer 1103 varies from that typically provided within the art, as the specific size requirements of the portable medical device and minimum inductance requirements of the USB power isolation chip impose constraints for the primary and secondary coils. In some embodiments a 12:9 core turns ratio is utilized along with at least one triple insulated wire. In a further embodiment, the transformer 1103 can be a toriod transformer. However, utilizing the aforementioned embodiments for the transformer and system design, constrains the low current (100 mA) loads at which the power isolation chip functions. This is because the power isolation chip draws less than 100 mA at an input voltage of 4.4V (low voltage) with a low output load current of 50 mA. The low output load current can then define the high output load current as 250 mA based on the USB specification current limitations of five times the low load current.

The board area illustrated in FIG. 11 can be formed with a stitched capacitance built into the circuit board, such that EMF emissions can be further controlled through attenuation of any high frequency noise provided during use of the infusion device. Each chip connection is shown including any additional circuitry that is utilized to power the portable medical device components while still meeting size and regulatory emission level constraints, such as IEC 60601-1 Safety Standards.

Figure 12:
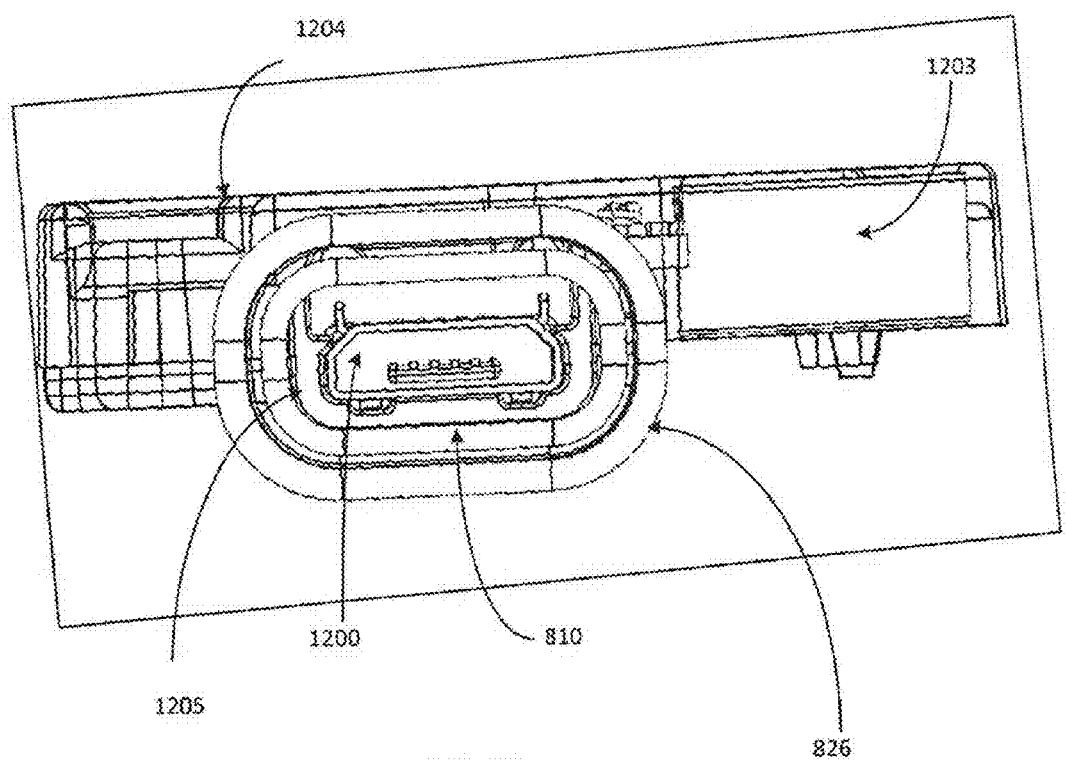
FIG. 12 is a schematic that depicts a front view of the electrical connector port and interface in FIG. 10.

FIG. 12 shows a front cross-sectional view of the electrical connector interface. An electrical connector port 1200 is securely fit into the housing of the portable medical device through the first, or outer o-ring 810. That is, the o-ring 810 is located closer to the outside of the device and is seated in the groove 820 of the USB port door. The inner, or primary o-ring 826 is located closer to the inner cavity of the device. The o-rings can be made of rubber or plastic polymer which is impermeable and can securely be fitted onto the respective locating surfaces 820, 828 (FIG. 8).

FIG. 12 shows that the overmold 1204 of the power isolation assembly is coupled to the electrical connector interface assembly. The coupling is in order to protect the user from experiencing any electrical shock or excessive radiation emissions during use of the portable medical device. The overmold 1204 can extend around, above and below the electrical connector interface assembly, such that any current drawn from a power source is isolated in the portable medical device prior to usage by, e.g., charging the battery or operating the inner components of the device. The overmold 1204 can extend across each component of the power isolation assembly, including the power isolation chip (not shown) and the transformer 1203. A molded structure 1205 can extend at least partially around the USC connector to protect the USB connector during the overmolding process.

Figure 13:
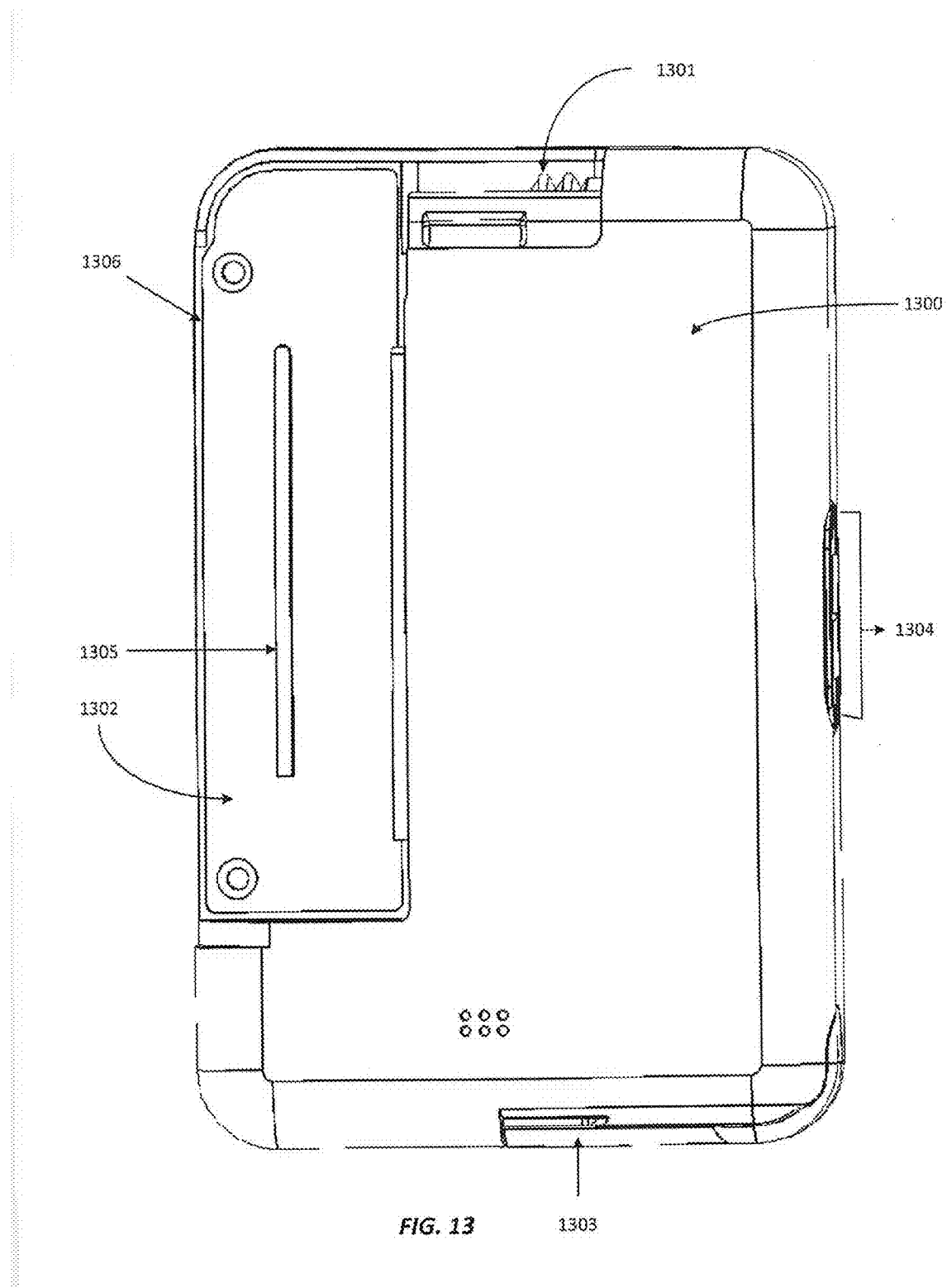
FIG. 13 is a schematic of a back view of a portable medical device, having the cartridge cover and pump cover removed.

Referring now to FIG. 13, a schematic illustrating the back view of the portable medical device is shown. The back view of the device illustrates a back plate 1300, a pumping mechanism 1301, a cartridge slot 1302, an input button 1304, and a electrical connector port door 1303. The back of the device is covered by a back plate 1300, which can be made of a durable plastic polymer or metal. The back plate 1300 can be semi-permanently attached to the device, such that removal is only achieved through use of an instrument or tool in order to protect the inner components of the portable medical device. The back plate 1300 can cover substantially all of the back of the portable medical device, except for a portion of the device which is capable of receiving a cartridge, such as an insulin cartridge. The back plate 1300 can be sealed along the outer walls of the portable medical device through a membrane or other form of sealant, which can prevent water and other elements (e.g., dust, liquids, etc.) from entering the device. In some embodiments, the outer walls of the device and the back plate of the device are formed as a single component. In other embodiments, the back plate 1300 is one of a plurality of components which, combined, comprise the housing of the portable medical device.

As previously mentioned, the back plate 1300 can exclude a portion under which an insulin cartridge is received. The cartridge slot 1302 can include a bump, or ridge 1305 onto which the cartridge can latch to be aligned in the cartridge slot 1302 to facilitate placement of the cartridge by a user of the portable medical device. In some embodiments, the ridge 1305 can instead be a groove, or ridge into which a cartridge can latch in order to be properly aligned. It should be understood that numerous variations to the design of the cartridge slot can be implemented, dependent on the size and shape of the cartridge. The cartridge of some embodiments fits securely into the cartridge slot, having minimal space around the perimeter of the cartridge and between the cartridge and cartridge slot 1302. The inner wall 1306 of the cartridge slot 1302 can include a membrane, which forms a water-tight seal around the cartridge slot 1302 when the cartridge door 1505 (shown in FIG. 15) is in place. Accordingly, the cartridge slot 1302 can include a locking mechanism, which allows the cartridge door to form a pressurized seal with the inner wall 1306 of the cartridge slot 1302.

Figure 14:
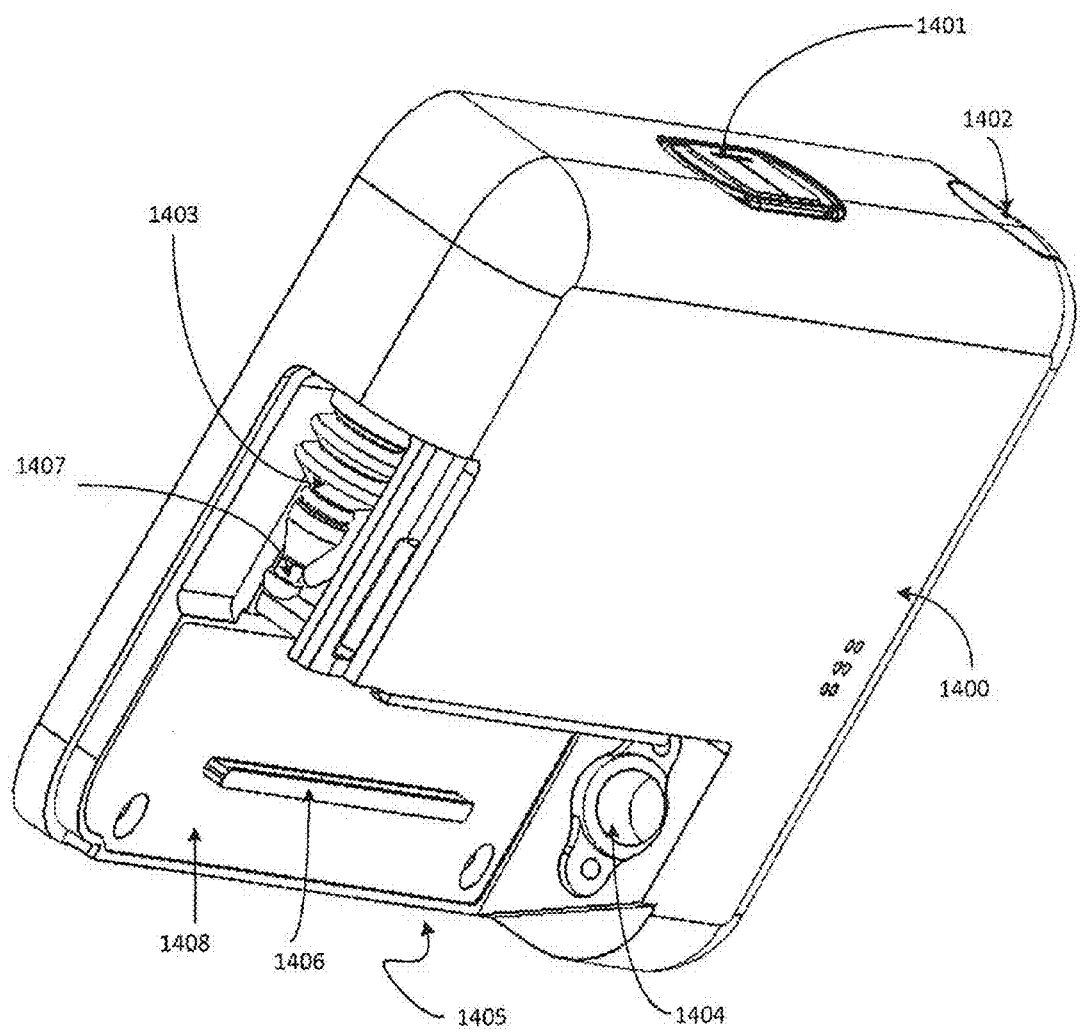
FIG. 14 is a schematic that depicts a perspective view of FIG. 13 in one embodiment.

Referring now to FIG. 14, a perspective view of the back and two side walls of the portable medical device is provided. The portable medical device as shown includes an input button 1401, a hinge portion of the electrical connector port door 1402, a back plate 1400, a cartridge slot 1405 for receiving an insulin cartridge, a ridge 1406 onto which the cartridge is hinged for alignment into the cartridge slot 1405, a cartridge receiving port 1404, which locks the cartridge into place within the cartridge slot 1405, and a cartridge slot backplate 1408. FIG. 14 also illustrates an open view of a pumping mechanism with the back plate 1400 removed. The pumping mechanism includes a rack pushrod 1407 that is utilized to compress the insulin cartridge and cause the insulin to move to the user through a tube or conduit such as a cannula (shown in FIG. 1). The pushrod can be made of a metal or other hard, non-pliable material capable of withstanding extreme temperatures and contact with liquids. The pushrod 1407 additionally includes a pushrod cover 1403, which is utilized to form an additional barrier between the pumping mechanism and the cartridge. The pushrod cover 1403 provides an additional layer of waterproofing to prevent any insulin leakage from the cartridge from entering the portable medical device and affecting the inner components. The pushrod cover 1403 can be made of a pliable plastic or rubber materials which can sustain repeated compression and expansion movements and which is impermeable to liquids. In some embodiments, an o-ring (not shown) can also be placed around the base of the pushrod 1407 and the top of the pushrod cover 1403 to prevent leakage into the portable medical device.

Figure 15:
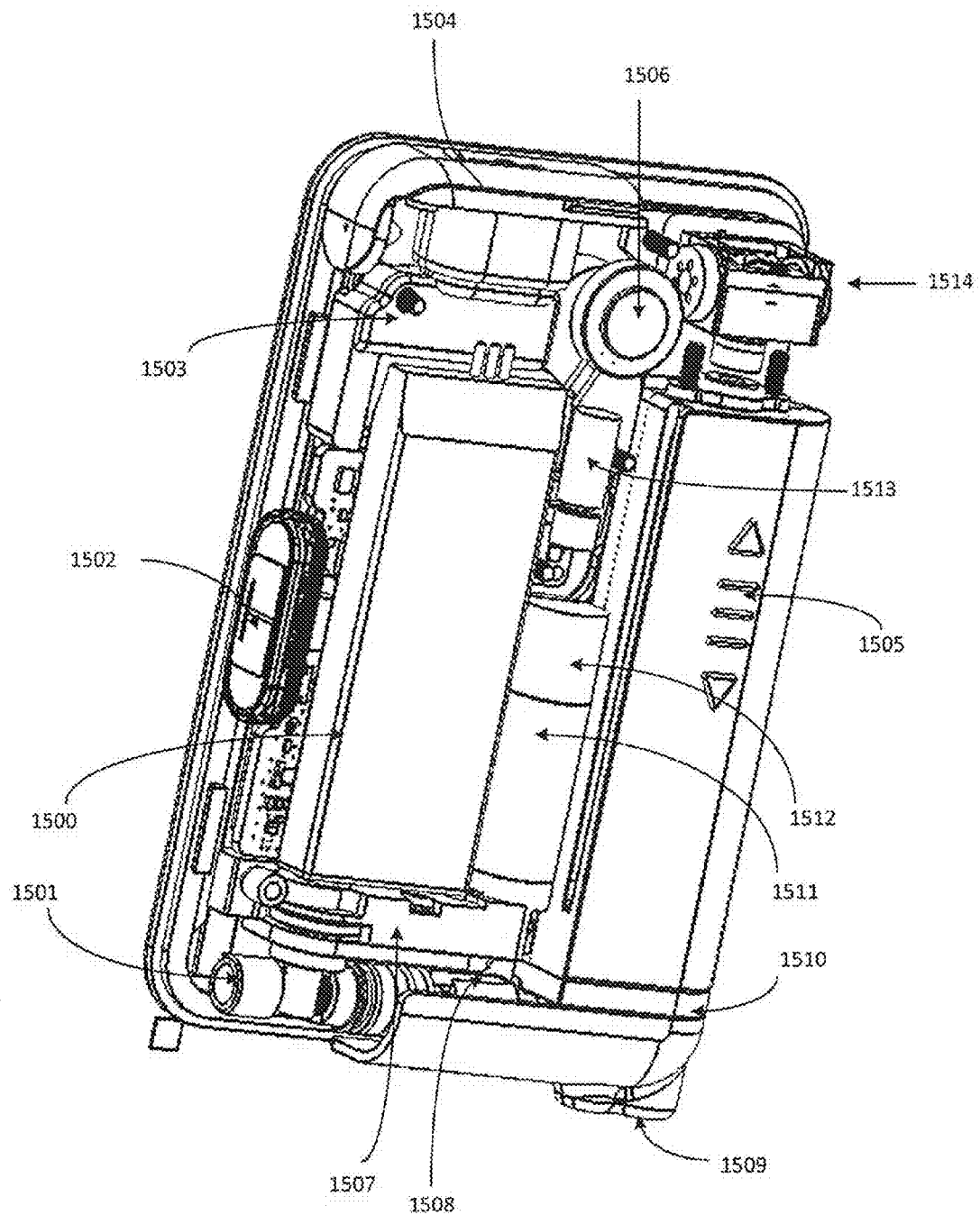
FIG. 15 is a schematic that depicts an alternative perspective view of FIG. 13, having the back face of the housing removed.

FIG. 15 shows a schematic view of the back of the portable medical device in FIG. 14 with the rear face removed. As shown in FIG. 15, the various elements controlled by the PCB on the front schematic view in FIG. 5 are provided. The device can include a speaker 1506 for providing alerts and other sounds indicating a function has been performed on the device. Additionally, the device can include a micro-valve assembly 1514, including, for example, a venting system and a thermal leak platform for the insulin cartridge. The insulin cartridge can be covered by a cartridge door 1505 and the housing of the portable medical device can include a cartridge shroud 1509 in which the connecting tube or cannula that delivers the insulin to the patient may be inserted.

Additionally, the device can include a power charging system that receives the controlled current from the power isolation chip. The power charging system may be used to charge a power storage cell such as a rechargeable battery 1500 of the portable medical device. Some embodiments may use a rechargeable battery such as a NiCad battery, LiPo battery, NiMH battery, or the like. The battery 1500 also can be a lithium ion (LiPo) battery or a similar type of battery known in the art that meets both the size and charge requirements of the portable medical device.

The operation for determining charging of the battery 1500 includes various steps which are dependent on the current battery charge and the current operating mode of the portable device. The portable medical device can be considered to be in different states (e.g., active mode, shelf mode) based on the charge level in the battery and the connection, or lack thereof, to a power supply source. The portable medical device first determines if a USB power supply is connected to the device. This determination may occur through the change in current detected as being supplied to both the isolated USB data control chip and the isolated USB power control chip. For example, an "always on" current sensor amplifier coupled to a Buck regulator can detect the current provided to the device by the connection to the power source. Two types of connections can be made to the power source. One is a configurable combined data/power source (e.g., a computer) and the other is a dedicated power-only source (e.g., a wall outlet). Depending on the calculated battery charge level and the mode of the system, each type of connection can determine a different type of power-up protocol and can determine how the battery on the device is charged.

After determining that a USB power supply has been connected through the USB interface (behind electrical connector port door 1504), the portable medical device next determines the type of source device supplying electrical power to the device. If the host power source is a dedicated power source, the electrical connector can supply a high mode current to the portable medical device and charge the battery at a faster rate. Being in a high rate battery charge does not necessarily signify that the portable medical device is in high or active mode.

The load output load current "low mode" charging, also referred to as suspended state or shelf mode, occurs when the portable medical device is plugged into a power source such as a desktop, laptop, or, e.g., tablet computer. That is, a power source that is not configured for high current connection with the portable medical device. As noted previously, the computer supplies only minimal power output (e.g., 100 mA) from the port interfaced with the power supply until a higher current output "high mode" (500 mA) can be negotiated, e.g., through configuration of the power supply. In some cases, if high current charging is requested before a connection port is configured with the power supply, the connection port will shut down and no current will be provided to the portable device.

The output of the transformer 1103 (shown in FIG. 11) supplies the aforementioned high mode or low mode current to a battery charger within the power isolation assembly 1503. The battery charger can be configured for use with the power supply and can include a charge current multiplier in order to charge a battery 1500 coupled to the battery charger even in low mode conditions. However, in order to supply the minimum amount of power to charge the battery 1500 and maintain the system components which inherently draw current and stay "always on," the power stored in the battery 1500 is monitored as well as the amount of power and current being supplied to the device during a charge condition, such as when the power supply is connected to a power supply source. The control of the power supply based on the current power within the battery 1500 is performed by a power control processor (see FIG. 11: 1102), which is coupled to the battery 1500 and battery charger within the power isolation assembly. The power control processor can control the power apportioned to the rest of the system components, such as a pump motor 1511, vibrate 1513, pump (rack bushing 1501, rack pushrod 1508 and gear box 1507), the output display screen, peripheral devices (e.g., Bluetooth), the data processor, and the like.

A data control processor may send requests to the power control processor due to an input from the user of the device. For example, if the user decides to remove and discontinue use of the device, the user may "power off" the device by depressing the input button 1502. If the shelf mode request is received by the power control processor, the power supplied to the data control processor is discontinued. The data control processor reads instructions stored in a memory element of the portable medical device for performing the functions of the components in the device, such as providing an output display (see FIG. 3: 302), a Bluetooth transmitter (see FIG. 5: 505), a speaker 1506, a motor 1511 controlling an insulin pump rack pushrod 1508 (e.g., through gears in gear box 1508), a touch control chip, and the like.

Removal of power will not delete data stored in the USB data isolation chip, nor will power removal eliminate the ability to charge, power up, or communicate with the data control processor. The data control processor typically remains in an "always on" condition, though the power supplied to the components performing the functions requested by the processor may no longer powered, such that the functionality of the data control processor is effectively terminated.

Figure 16A:
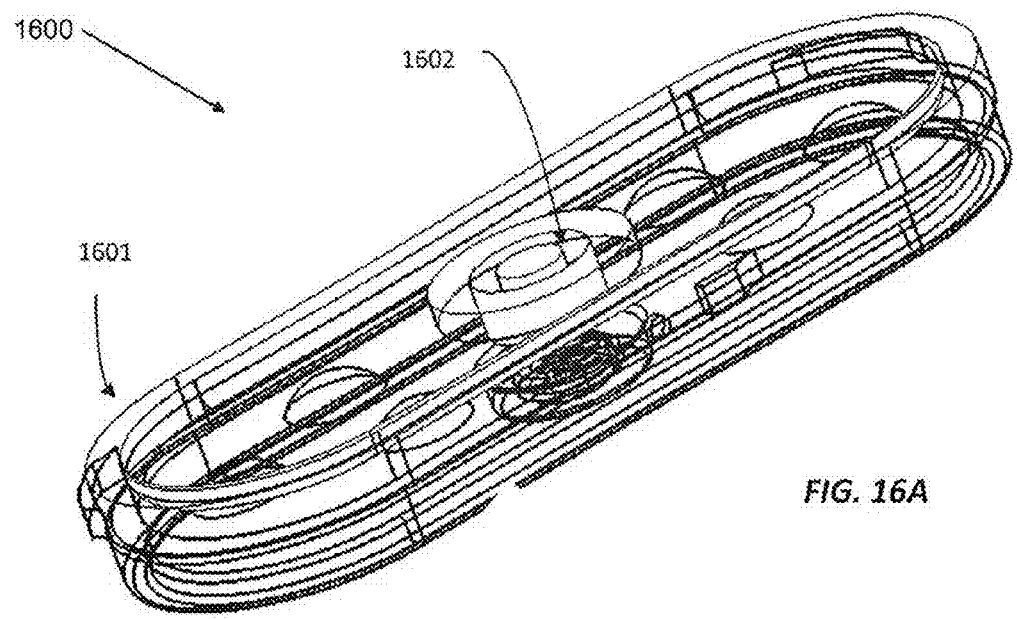
FIG. 16A-16C are schematics of various views of an input button shown in FIG. 15
Figure 16B:
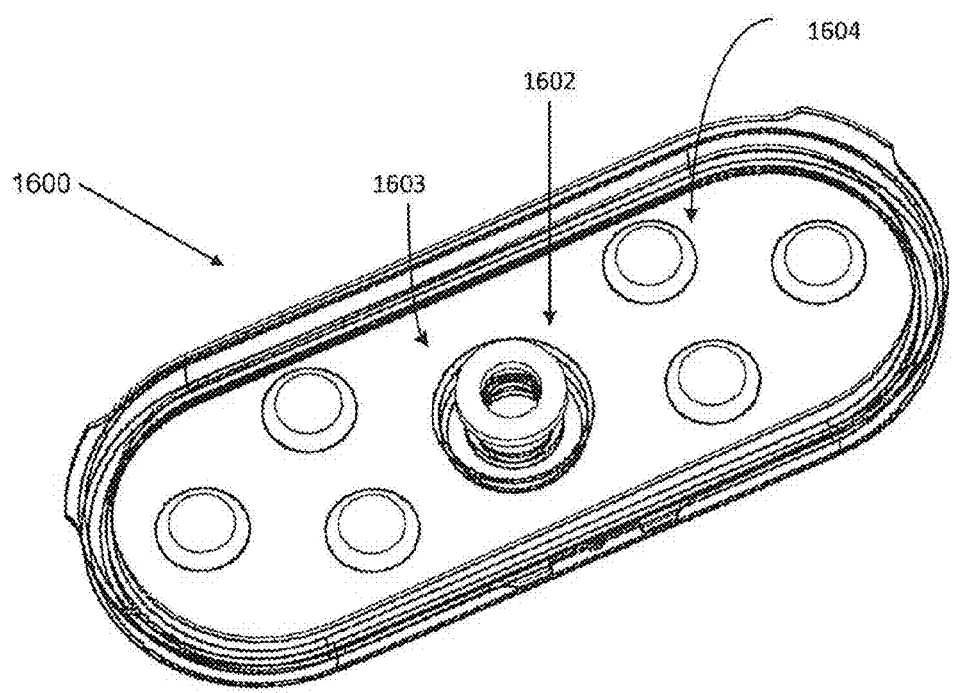
Figure 16C:
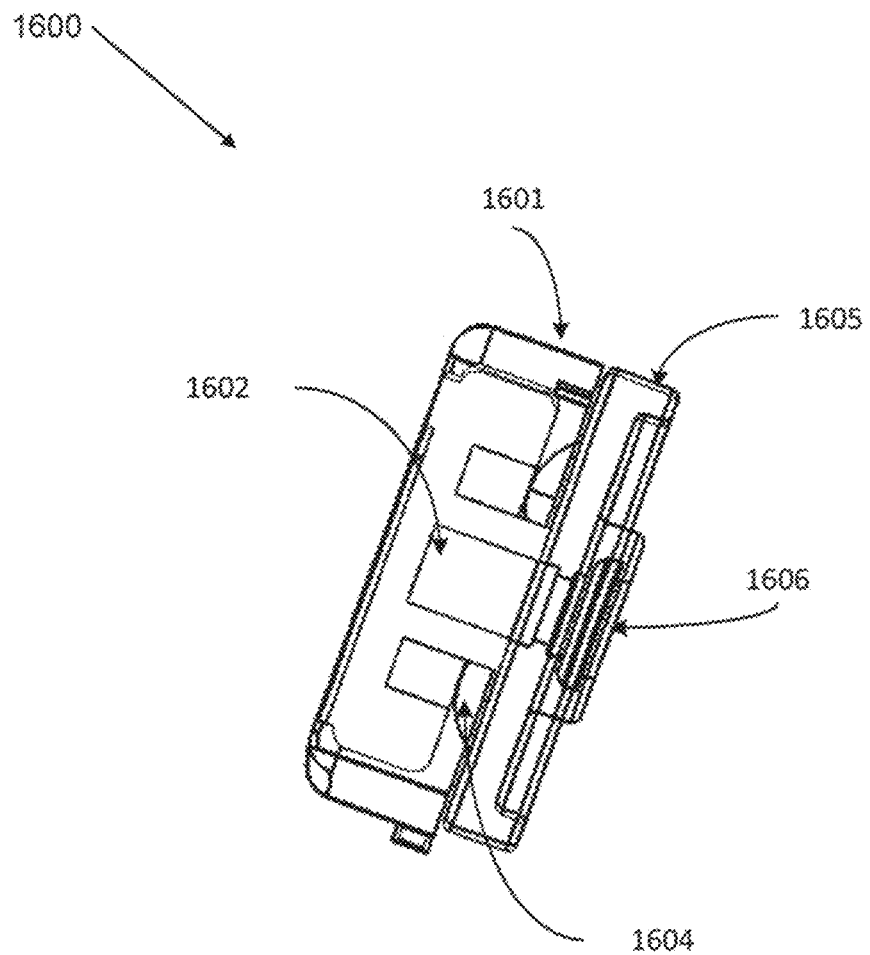

Referring now to FIGS. 16A-16C, exemplary schematic views of a waterproof input button 1600 are illustrated. As shown in FIG. 16A, a skeleton view of the outer shell 1601 of the button and the inner components of the input mechanism 1602 are illustrated. The housing, or outer shell 1601, of the button 1600 can be made of a plastic or other polymer in a pre-formed shape and the side walls can be collapsible such that the input button can be depressed by a user. The outer shell 1601 can additionally be made of a non-permeable soft material, such as a dense rubber. The input mechanism 1602 can be located within a central opening of the outer shell 1601, such that when a user erroneously depresses another area, e.g., side, of the input button, an input is not received.

FIG. 16B shows a top view of the input button. The input button can have a backplate 1603, which sits adjacent to the side wall of the portable medical device (e.g., element 1304 in FIG. 13). The backplate 1603 can be made of a hard polymer in order to prevent any voltage leakage from the device during user interaction. Additionally, the backplate can form a protective barrier as a portion of the side wall of the housing of the portable medical device. The backplate can include several soft ridges or bumps 1604 that can absorb the pressure of the input button during depression by the user, such that the input mechanism is not damaged, e.g., due to excessive force during depression, and such that the top portion of the housing, or outer shell 1601, and the backplate 1603 do not collide. The bumps 1604 absorb shock and can be made of a rubber or other force-absorbing non-permeable material. The bumps 1604 can protrude through pre-formed openings in the backplate 1603 or can be formed with the backplate 1603 or on the top plane of the backplate 1603. The input mechanism 1600 can include a spring type assembly, such that when the input button is depressed, the button returns to its original position.

FIG. 16C shows a cross-sectional view of the button. The input mechanism 1600 extends through the button housing 1601 to a base point 1606, which provides a contact point to the PCB within the portable medical device to communicate a signal to wake the device. The base 1605 of the input button can be formed from a membrane that is impermeable to water and other liquids. The base 1605 can be formed with the bumps 1604 in order to prevent any liquid from entering the device. Accordingly, the base 1605 can cover a portion of the side wall of the portable medical device on which the input button is located and can form a seal between the input button housing 1601 of the portable medical device and the inner components.

Although the aforementioned description specifically describes a portable medical device for administering insulin to a patient, it should be understood that such a device is only one embodiment of the invention. The device can also include any portable device having a display and a processor. For example, the device can include a mobile computing device, such as a Smartphone. In one embodiment, such a device can be used to remotely control a portable medical device as described herein. Alternatively, a portable medical device as described herein may be controlled by a dedicated remote control specifically designed for use with the device.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments herein. Accordingly, it is not intended that the invention be limited by the forgoing detailed description.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion pump, comprising:
   a housing having a front surface and a back surface that are spaced apart and enclosed by side surfaces to define an internal cavity;
   an electrical connector port fitted to the housing and extending into the internal cavity, the electrical connector port operably connected to a power isolation connector and a data isolation connector disposed within the housing, the electrical connector port adapted to receive electrical power and data via a direct electrical connection, and to direct the electrical power to the power isolation connector and the data to the data isolation connector,
   an overmold mechanically coupled to the housing and having an upper portion and a lower portion, wherein the electrical connector port is disposed between the upper portion and the lower portion such that the overmold physically separates the electrical connector from the housing, and wherein the overmold, the housing, and the electrical connector port are configured to provide a seal preventing passage of moisture into the internal cavity;
   a transformer disposed within the overmold and configured to control electrical input from the electrical connector port; and
   a battery charger disposed within the overmold and configured to receive substantially constant output from the transformer.

2. The ambulatory infusion pump of claim 1, further comprising an electrical connector port door configured to be attached to the housing over the electrical connector port.

3. The ambulatory infusion pump of claim 2, wherein a seal is formed between the electrical connector port and the electrical connector port door.

4. The ambulatory infusion pump of claim 3, wherein the overmold comprises an insulator material having a shape determined by the power isolation connector and associated circuitry in order to meet regulatory emissions requirements for a medical device.

5. The ambulatory infusion pump of claim 4, wherein the overmold comprises a membrane.

6. The ambulatory infusion pump of claim 1, wherein the power isolation connector is electrically isolated from the data isolation connector.

7. The ambulatory infusion pump of claim 1, further comprising:
   a processor disposed in the housing; and
   a touch sensitive display screen, wherein the processor is capable of receiving inputs from the touch sensitive display screen.

8. An ambulatory infusion pump, comprising:
   a housing having a front surface and a back surface that are spaced apart and enclosed by side surfaces to define an internal cavity;
   an electrical connector port fitted to the housing and extending into the internal cavity, the electrical connector port operably connected to a power isolation connector and a data isolation connector disposed within the housing, the electrical connector port adapted to receive electrical power and data via a direct electrical connection, and direct the electrical power to the power isolation connector and the data to the data isolation connector;
   an overmold mechanically coupled to the housing and having an upper portion and a lower portion, wherein the electrical connector port is disposed between the upper portion and the lower portion such that the overmold physically separates the electrical connector from the housing, and wherein the overmold, the housing, and the electrical connector port are configured to provide a seal preventing passage of moisture into the internal cavity, and wherein the power isolation connector is coupled to a power isolation circuit;
   a transformer disposed within the overmold and configured to control electrical input from the electrical connector port; and
   a battery charger disposed within the overmold and configured to receive substantially constant output from the transformer.

9. The ambulatory infusion pump of claim 8, further comprising an electrical connector port door configured to be attached to the housing over the electrical connector port.

10. The ambulatory infusion pump of claim 9, wherein a seal is formed between the electrical connector port and the electrical connector port door.

11. The ambulatory infusion pump of claim 10, wherein the overmold comprises an insulator material having a shape determined by the power isolation connector and associated circuitry in order to meet regulatory emissions requirements for a medical device.

12. The ambulatory infusion pump of claim 8, wherein the overmold is comprised of a non-conductive material.

13. The ambulatory infusion pump of claim 8, wherein the power isolation connector is electrically isolated from the data isolation connector.

14. The ambulatory infusion pump of claim 8, further comprising:
   a processor disposed in the housing; and
   a touch sensitive display screen, wherein the processor is capable of receiving inputs from the touch sensitive display screen.

* * * * *